United States Patent
Jan et al.

(10) Patent No.: US 7,268,267 B2
(45) Date of Patent: *Sep. 11, 2007

(54) ALKYLATION PROCESS USING UZM-8 ZEOLITE

(75) Inventors: Deng-Yang Jan, Elk Grove Village, IL (US); James A. Johnson, Clarendon Hills, IL (US); Robert J. Schmidt, Barrington, IL (US); Guy B. Woodle, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 120 days.

This patent is subject to a terminal disclaimer.

(21) Appl. No.: 11/170,420

(22) Filed: Jun. 29, 2005

(65) Prior Publication Data

US 2006/0224031 A1 Oct. 5, 2006

Related U.S. Application Data

(63) Continuation-in-part of application No. 10/828,989, filed on Apr. 21, 2004, now Pat. No. 7,091,390, which is a continuation-in-part of application No. 10/395,466, filed on Mar. 21, 2003, now Pat. No. 6,756,030, and a continuation-in-part of application No. 10/395,624, filed on Mar. 21, 2003, now abandoned.

(51) Int. Cl.
*C07C 2/66* (2006.01)

(52) U.S. Cl. .................................................. 585/467

(58) Field of Classification Search ................. 585/467
See application file for complete search history.

(56) References Cited

U.S. PATENT DOCUMENTS

| | | | |
|---|---|---|---|
| 5,877,370 A | 3/1999 | Gajda | 585/467 |
| 6,043,402 A | 3/2000 | Gajda | 585/467 |
| 6,479,721 B1 | 11/2002 | Gajda et al. | 585/467 |
| 6,756,030 B1 | 6/2004 | Rohde et al. | 423/718 |
| 6,835,862 B1 | 12/2004 | Gajda et al. | 585/467 |

*Primary Examiner*—Thuan Dinh Dang
(74) *Attorney, Agent, or Firm*—James C. Paschall; David J. Piasecki

(57) ABSTRACT

A process for the alkylation of aromatics with olefins using a solid catalyst bed containing UZM-8 zeolite is disclosed. A polyalkylated aromatic is passed to the catalyst bed to reduce the concentration of the olefin at alkylation conditions. A portion of the effluent recovered from the catalyst bed may be recycled to the catalyst bed. Such operation can decrease the catalyst deactivation rate and the formation of diphenylalkanes. The process disclosed herein is applicable to processes for the production of a wide variety of commercially important alkylated aromatics, including ethylbenzene and cumene.

25 Claims, 9 Drawing Sheets

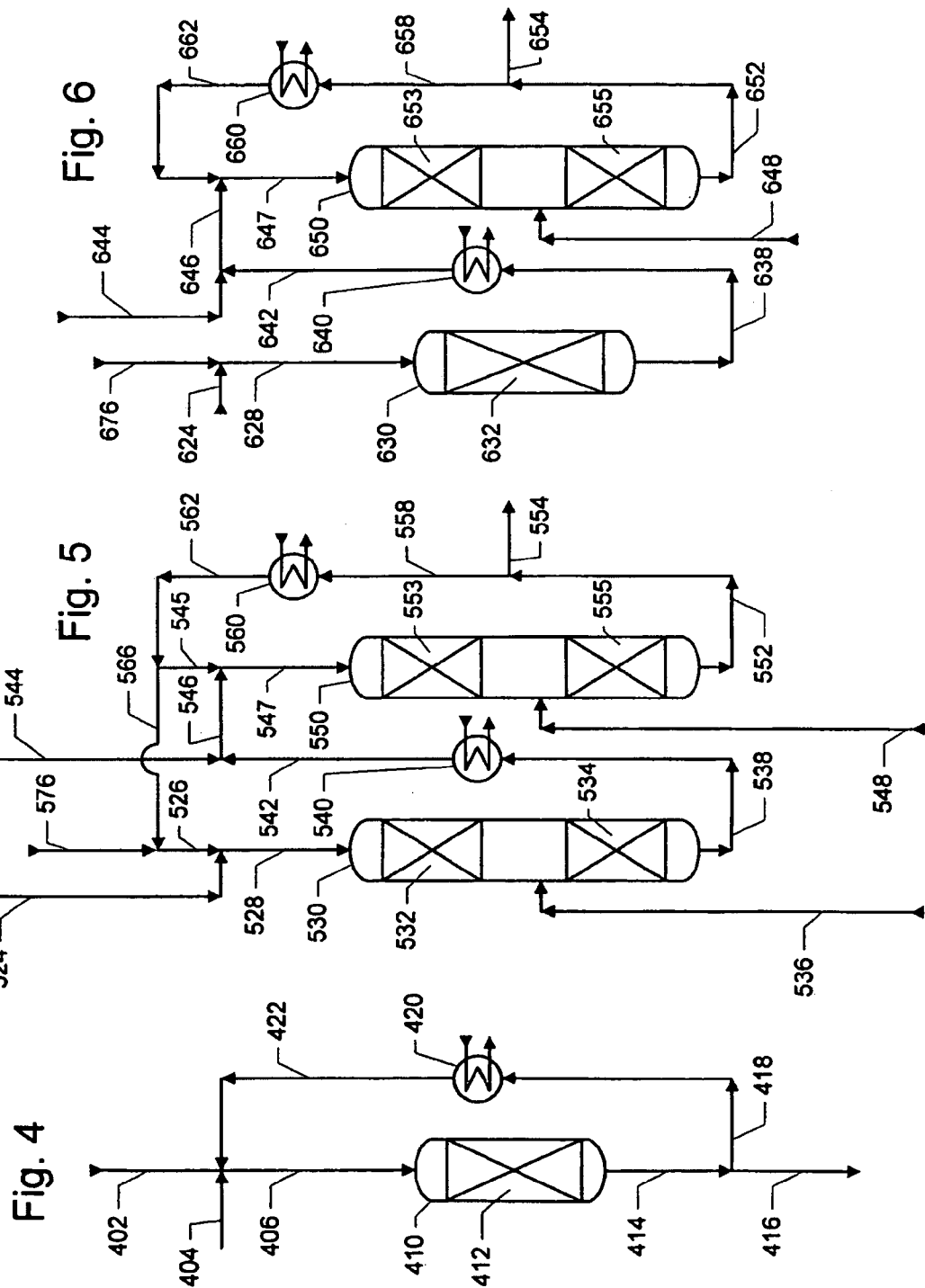

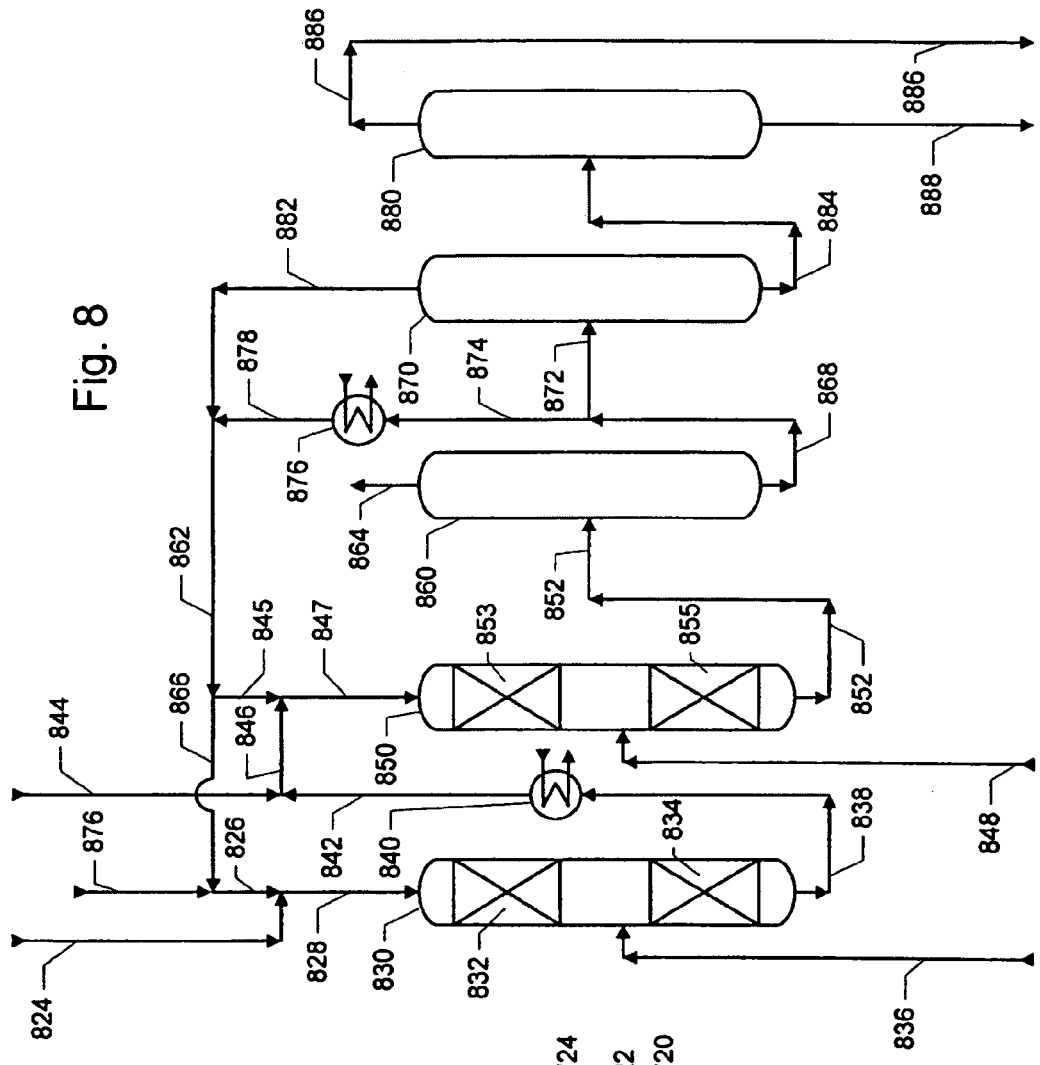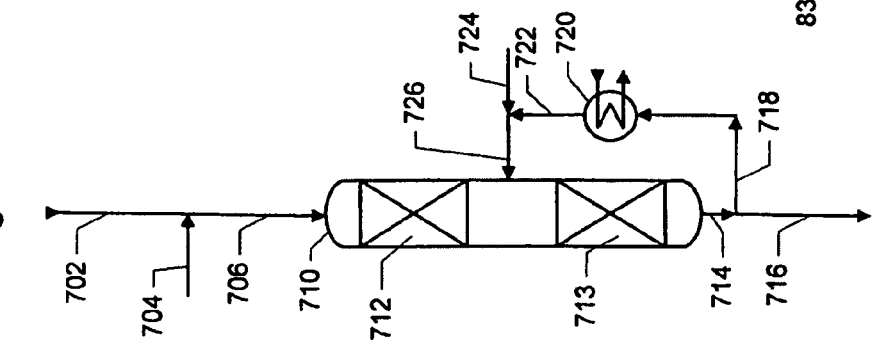

ALKYLATION PROCESS USING UZM-8 ZEOLITE

CROSS-REFERENCE TO RELATED APPLICATION

This application is a Continuation-In-Part of application Ser. No. 10/828,989, filed Apr. 21, 2004 and now U.S. Pat. No. 7,091,390, the contents of which are hereby incorporated by reference in its entirety, which is a Continuation-in-Part of application Ser. No. 10/395,466, filed Mar. 21, 2003 and now U.S. Pat. No. 6,756,030, the contents of which are hereby incorporated by reference in its entirety, and of application Ser. No. 10/395,624, filed Mar. 21, 2003 (now abandoned), the contents of which are hereby incorporated by reference in its entirety.

FIELD OF THE INVENTION

This invention relates to a process for producing monoalkylated aromatic compounds by alkylation. Specifically, this invention relates to highly-selective alkylation and transalkylation to produce cumene and ethylbenzene.

BACKGROUND OF THE INVENTION

Alkylation of aromatic compounds with a $C_2$ to $C_4$ olefin and transalkylation of polyalkylaromatic compounds are two common reactions for producing monoalkylated aromatic compounds. Examples of these two reactions that are practiced industrially to produce ethylbenzene are the alkylation of benzene with ethylene and the transalkylation of benzene and a diethylbenzene. A simplified summary of the alkylation reaction and its common product and byproducts is given below:

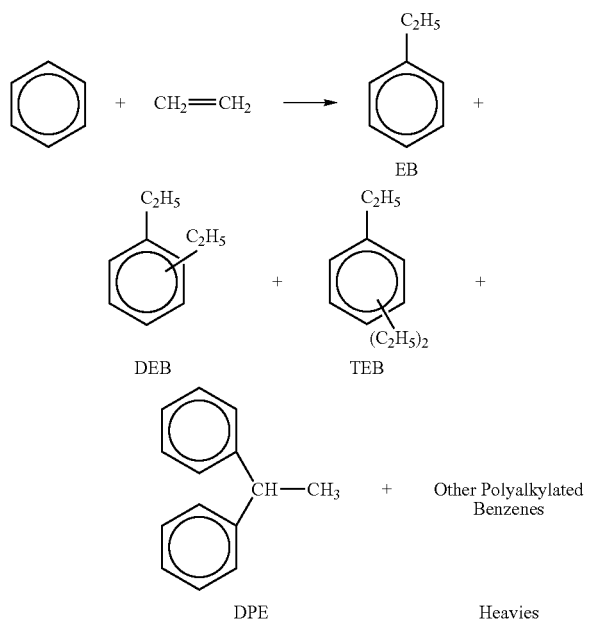

In addition to these byproducts, the $C_2$-$C_4$ olefin can dimerize to form a $C_4$-$C_8$ olefin or oligomerize to form a $C_6$-$C_{12}$ olefin. These higher olefins can in turn react with benzene to form alkylbenzenes having alkyl groups with 4 to 12 carbon atoms, such as butylbenzenes, hexylbenzenes, octylbenzenes, and dodecylbenzenes. These heavy alkylbenzenes can themselves be further alkylated to form other heavy polyalkylated benzenes.

Although the formation of the diethylbenzene, triethylbenzene, and tetraethylbenzene (TeEB) isomers might, at first glance, be viewed as byproducts that represent a reduction in the efficient utilization of ethylene, in fact each can be readily transalkylated by benzene to produce ethylbenzene, as shown below:

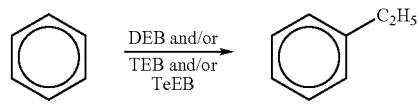

Combining alkylation and transalkylation can thus maximize ethylbenzene production. Such a combination can be carried out in a process having two reaction zones, one for alkylation and the other for transalkylation, or in a process having a single reaction zone in which alkylation and transalkylation both occur. In many cases, a single reaction zone is preferred over two reaction zones because of the savings in capital investment.

One disadvantage of alkylation-transalkylation processes, regardless of whether the alkylation and transalkylation reactions occur in the same or separate reaction zones, is that byproduct 1,1-diphenylethane (1,1-DPE) can not be readily converted to ethylbenzene by alkylation or transalkylation. Similarly, byproduct alkylbenzenes formed from a dimerized or oligomerized olefin, such as butylbenzenes, hexylbenzenes, octylbenzenes, and dodecylbenzenes can not be converted to ethylbenzene by alkylation or transalkylation. These byproducts represent a reduction in ethylene utilization efficiency and a loss of ethylene. In fact, the byproduction of 1,1-DPE, as well as of the heavier polyethylated benzenes other than diethylbenzene and triethylbenzene, and of the butylbenzenes and octylbenzenes represents virtually all of the reduction in the ethylene utilization efficiency and a loss of benzene as well. As used herein, the term "heavies" refers to polyalkyl aromatics other than dialkyl and trialkyl and tetraalkyl aromatics where the alkyl group has the same number of carbon atoms as the feed olefin, to alkylaromatics formed from dimerized or oligomerized olefins such as butylbenzenes when the olefin is ethylene, and to other even heavier alkylation and transalkylation byproducts including diphenylalkanes (DPA) and alkylated diarylalkanes (DAAs), such as diphenylethanes (DPEs), alkylated diarylethanes (DAEs), diphenylpropane (DPP), and alkylated diarylpropanes (DAPs). The current minimum requirement for combination processes is that 1,1-DPE be not more than 1.0 wt-% relative to ethylbenzene. The formation of 1,1-DPE itself is assuming added importance and significance in view of the expectation in some areas of near-term minimum standards for the content of 1,1-DPE of not more than 0.5 wt-%.

In reaction zones where alkylation and transalkylation occur to produce a monoalkylated aromatic, a key operating variable is the molar ratio of aryl groups per alkyl group. The numerator of this ratio is the number of moles of aryl groups passing through the reaction zone during a specified period of time. The number of moles of aryl groups is the sum of all aryl groups, regardless of the compound in which the aryl group happens to be. In the context of ethylbenzene production, for example, one mole of benzene, one mole of ethylbenzene, and one mole of diethylbenzene each contribute one mole of aryl group to the sum of aryl groups. The denominator of this ratio is the number of moles of alkyl groups that have the same number of carbon atoms as that of the alkyl group on the desired monoalkylated aromatic and which pass through the reaction zone during the same specified period of time. The number of moles of alkyl groups is the sum of all alkyl and alkenyl groups with the same number of carbon atoms as that of the alkyl group on the desired monoalkylated aromatic, regardless of the compound in which the alkyl or alkyl group happens to be, except that paraffins are not included. In the context of ethylbenzene production, the number of moles of ethyl groups is the sum of all ethyl and ethenyl groups, regardless of the compound in which the ethyl or ethenyl group happens to be, except that paraffins, such as ethane, propane, n-butane, isobutane, pentanes, and higher paraffins are excluded from the computation of the number of moles of ethyl groups. For example, one mole of ethylene and one mole of ethylbenzene each contribute one mole of ethyl group to the sum of ethyl groups, whereas one mole of diethylbenzene contributes two moles of ethyl groups and one mole of triethylbenzene contributes three moles of ethyl groups. Butylbenzene and octylbenzene contribute no moles of ethyl groups In response to the hydrocarbon processing industry's demands for lower molar ratios of aryl groups per alkyl group and more efficient utilization of feed olefins, improved processes for the production of alkylbenzenes are sought.

SUMMARY OF THE INVENTION

A process has been discovered to significantly reduce the formation of diphenylalkanes and/or alkyl aromatics with alkyl groups corresponding to dimerized or oligomerized feed olefin in an alkylation process to produce alkyl aromatics, such as ethylbenzene and cumene, by alkylation using solid catalysts containing UZM-8 zeolite. The process disclosed herein is particularly useful at a low molar ratio of aryl groups per $C_2$-$C_4$ alkyl group, such as 6 or less. The process passes a feed aromatic, a $C_2$-$C_4$ olefin, and an alkylated derivative of the feed aromatic to an alkylation catalyst bed containing UZM-8 zeolite. The concentration of the $C_2$-$C_4$ olefin based on the weight of the feed aromatic, the $C_2$-$C_4$ olefin, and the alkylated derivative of the feed aromatic passed to the UZM-8 zeolite bed can be relatively high, such as at most 17 wt-%, at most 10 wt-%, or at most 5 wt-%. The concentration of the $C_2$-$C_4$ olefin may preferably be positive and near zero in circumstances, but minimum concentrations of 0.1 wt-% or 1.5 wt-% may also be used. The alkylated derivative of the feed aromatic may have from one to six more $C_2$-$C_4$ alkyl groups than the feed aromatic, and preferably the alkylated derivative is a dialkylated or trialkylated derivative of the feed aromatic. The alkylated derivative may be introduced to the UZM-8 zeolite bed in any process stream, and preferably the stream is an aliquot recycled portion of the UZM-8 zeolite bed effluent. A relatively low amount of the aliquot portion of the effluent may be used, such as a ratio of the weight of the aliquot portion to the combined weight of the feed aromatic and the $C_2$-$C_4$ olefin of at least 0.1. Higher ratios of at least 1.0, 2.5, or 4.0 can also be used. This result using a solid catalyst comprising UZM-8 zeolite was surprising. UZM-8 zeolite has a unique layered structure, and its performance was not predictable from the prior art zeolites such as beta, omega, ZSM-5, PSH-3, MCM-22, MCM-36, MCM-49, and MCM-56.

An alkylation process of alkylating benzene with ethylene, propylene, or butene using effluent recycle shows a significant selectivity advantage if UZM-8 zeolite is used instead of a zeolite used in prior art processes. By using the process disclosed herein, ethylbenzene and cumene processes can now minimize formation of 1,1-DPE and/or other undesired byproducts even while operating profitably at low molar ratios of aryl groups per ethyl group.

Without limiting the process disclosed herein to any particular theory, a working hypothesis may in part explain the observed results. It is believed the unique layered structure of UZM-8 zeolite makes available a relatively large number of catalytically active sites near or on the surface of the UZM-8 zeolite. Once monoalkylation at an active site, the resulting monalkylated aromatic can be readily removed from the surface. This reduces the formation of polyalkylated and heavier byproducts. Using effluent recycle with UZM-8 zeolite facilitates the transport of the monoalkylated aromatic from the active site. This working hypothesis explains the decreased formation of diarylalkanes and other byproducts when alkylating aromatics with ethylene, propylene, butenes, and higher olefins. For example, with ethylene alkylating benzene less 1,1-DPE and butylbenzenes would form. Where the olefin is propylene for instance, less 2,2-diphenylpropane (2,2-DPP) and hexylbenzenes would form, and possibly less 1,1-diphenylpropane (1,1-DPP) too. In the case where the olefin is butene, less diphenylbutanes and butylbenzenes would form.

Other embodiments of the process disclosed herein are described in the detailed description of the invention.

INFORMATION DISCLOSURE

U.S. Pat. No. 6,835,862 B1, the teachings of which are hereby incorporated herein in its entirety, describes a process for producing a monoalkylated aromatic such as ethylbenzene that comprises comprising passing an aromatic feedstock comprising a feed aromatic such as benzene, an olefinic feedstock comprising a feed olefin such as ethylene, and a first aliquot portion of an effluent stream to an alkylation catalyst bed containing a solid catalyst. The solid catalyst comprises a zeolite selected from the group consisting of zeolite beta, omega, ZSM-5, PSH-3, MCM-22, MCM-36, MCM-49, and MCM-56. The ratio of the weight of the first aliquot portion per unit time to the sum of the weights of the aromatic feedstock and the olefinic feedstock per said unit time is more than 2.5. An effluent stream comprising the monoalkylated aromatic is withdrawn from the alkylation catalyst bed, and the effluent stream contains less than 1.0 wt-% diarylalkane relative to the monoalkylated aromatic.

U.S. Pat. No. 5,877,370, the teachings of which are hereby incorporated herein in its entirety, describes a reduction in the amount of 1,1-DPE formed in the production of ethylbenzene. The highest ratio of weight of recycle effluent per weight of fresh benzene that U.S. Pat. No. 5,877,370 teaches is 3 (Example 10, Table 3) which, at a phenyl/ethyl molar ratio of 5.0, corresponds to a ratio of weight of recycle effluent per weight of fresh feed (i.e., fresh benzene and fresh olefin) of 2.5.

U.S. Pat. No. 6,756,030 B1, the teachings of which are hereby incorporated herein in its entirety, describes UZM-8 and its preparation and use.

BRIEF DESCRIPTION OF THE DRAWINGS

FIGS. 1-8 are schematic illustrations of embodiments of the process disclosed herein.

DETAILED DESCRIPTION OF THE INVENTION

Figure 1:
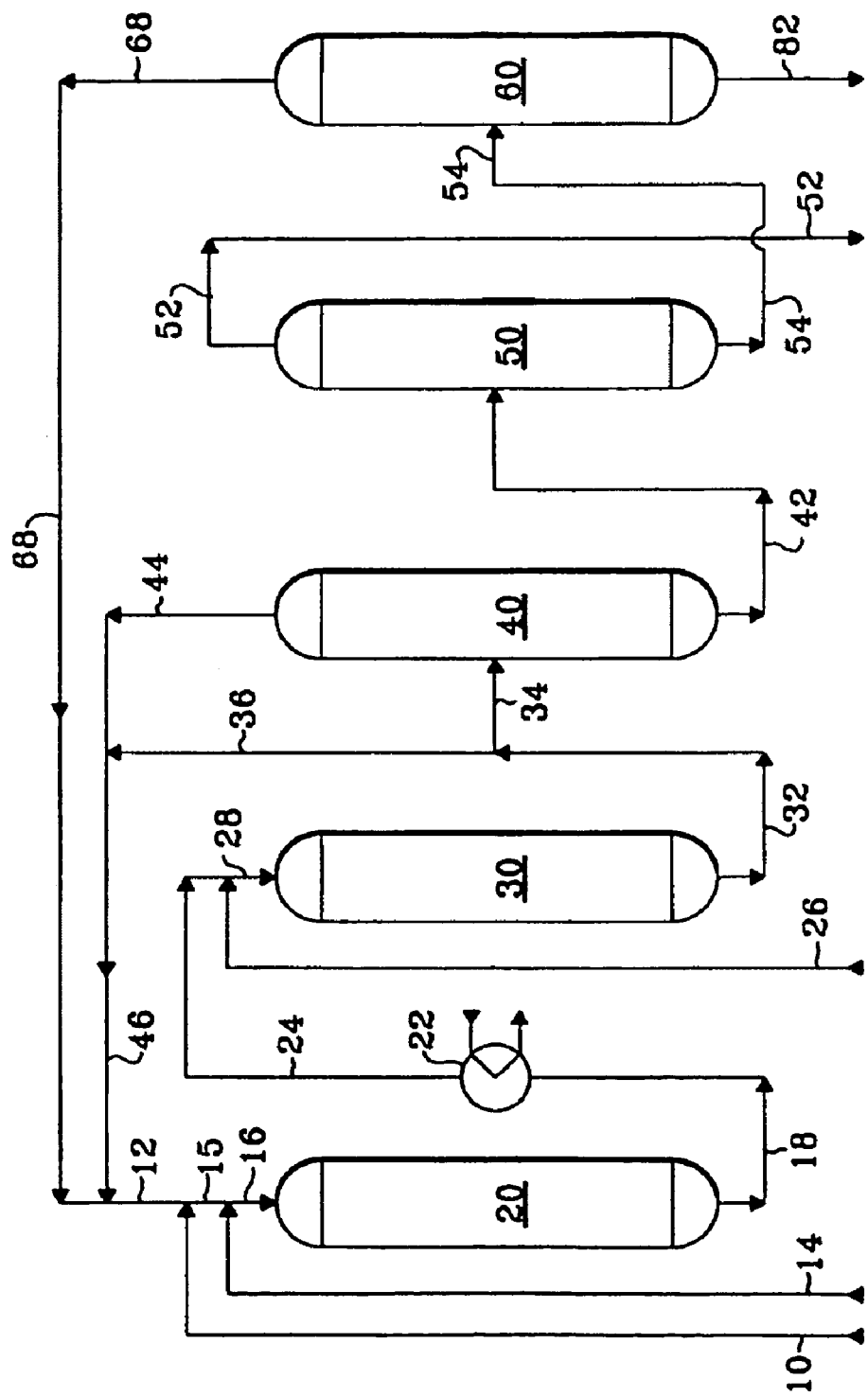

The process disclosed herein can be expected to be applicable generally to the alkylation of an alkylation substrate with an alkylation agent. The process disclosed herein is more specifically applicable to the production of an alkyl aromatic by alkylation of a feed aromatic with a feed olefin. Although benzene is the principal feed aromatic of interest, feed aromatics such as alkyl-substituted benzenes, condensed ring systems generally, and alkylated derivatives thereof may be used. Examples of such feed aromatics are toluene, ethylbenzene, propylbenzene, and so forth; xylene, mesitylene, methylethylbenzene, and so on; naphthalene, anthracene, phenanthrene, methylnaphthalene, dimethylnaphthalene, and tetralin. More than one feed aromatic can be used. The feed aromatic may be introduced into an alkylation catalyst bed in one or more aromatic feed stream. Each aromatic feed stream may contain one or more feed aromatics. Besides the feed aromatic(s), an aromatic feed stream may contain non-aromatics, including but not limited to saturated and unsaturated cyclic hydrocarbons that have the same, one more, or one less, number of carbon atoms as the feed aromatic. For example, an aromatic feed stream containing benzene may also contain cyclohexane, cycloheptane, cyclohexenes, or cycloheptenes, as well as methylated versions of any of these hydrocarbons, or mixtures thereof. The concentration of each feed aromatic in each aromatic feed stream may range from 0.01 to 100 wt-%.

Feed olefins containing from 2 to 6 carbon atoms are the principal alkylating agents contemplated for the process disclosed herein. Examples of such feed olefins include $C_2$-$C_4$ olefins, namely ethylene, propylene, butene-1, cis-butene-2, trans-butene-2, and iso-butene. However, feed olefins having from 2 to 20 carbon atoms may be used effectively in the process disclosed herein. More than one feed olefin may be used. The feed olefin may be introduced into an alkylation catalyst bed in one or more olefinic feed streams. Each olefinic feed stream may contain one or more feed olefins. In addition to the feed olefin(s), an olefinic feed stream may contain non-olefins, such as paraffins that have the same number of carbon atoms as the olefin. For example, a propylene-containing olefinic feed stream may also contain propane, while an olefinic feed stream containing ethylene may also contain ethane. The concentration of each feed olefin in each olefinic feed stream may range from 0.01 to 100 wt-%.

The most widely practiced hydrocarbon conversion processes to which the present invention is applicable are the catalytic alkylation of benzene with ethylene to produce ethylbenzene, the catalytic alkylation of benzene with propylene to produce cumene, and the catalytic alkylation of benzene with butene to produce butylbenzene. Although the discussion herein of the present invention will occasionally refer to a catalytic cumene reaction system, the discussion mainly is in reference to its application to a catalytic ethylbenzene reaction system. It is not intended that this discussion limit the scope of the present invention as set forth in the claims.

In practicing the process disclosed herein, a portion of the effluent of the alkylation reaction zone is reintroduced into the alkylation reaction zone. Unless otherwise noted in this specification, the term "portion"—when describing a process stream—refers to either an aliquot portion of the stream or a dissimilar fraction of the stream having a different composition than the total stream from which it was derived. An aliquot portion of the stream is a portion of the stream that has essentially the same composition as the stream from which it was derived. In some embodiments of the process disclosed herein, the reintroduced portion of the alkylation reaction zone effluent may contain a transalkylation agent. Consequently, in practicing these embodiments of the process disclosed herein a transalkylation agent is introduced into the alkylation reaction zone with the alkylation effluent. In other embodiments of the process disclosed herein, the transalkylation agent may be introduced via a stream other than a portion of the alkylation effluent stream. In theory, the transalkylation agent, if present, may be any compound that is capable of transalkylating with the alkylation substrate (e.g., benzene), mixing with the alkylating agent (e.g., ethylene), and decreasing the concentration of the alkylating agent at and downstream of the alkylation agent injection point. In practice, however, the transalkylation agent preferably has a number of characteristics that are consistent with the process objective of producing high yields of high-purity product ethylbenzene. First, the transalkylation agent should increase ethylbenzene yield by transalkylation, in addition to increasing ethylbenzene yield by minimizing 1,1-DPE formation. Accordingly, a polyethylbenzene, such as diethylbenzene, triethylbenzene, and so forth up to even hexaethylbenzene, is preferred because each can transalkylate to ethylbenzene, regardless of whether each is alkylated by ethylene. Because of the possibility of alkylation of the polyethylbenzene by ethylene, however, the lighter polyethylbenzenes are more preferred over the heavier polyethylbenzenes, with diethylbenzene being most preferred. More generally when alkylating a feed aromatic with a $C_2$-$C_4$ olefin, the transalkylation agent is an alkylated derivative of the feed aromatic having from one to six more $C_2$-$C_4$ alkyl groups than the feed aromatic.

A second characteristic of the transalkylation agent is that the transalkylation agent preferably decreases the molar ratio of aryl groups per alkyl groups in the alkylation reaction zone. This is usually not a limiting characteristic, however, because if the transalkylation agent has at least one aryl group and one alkyl group, then the transalkylation agent will decrease the molar ratio of aryl groups per alkyl group if the ratio is greater than 1. Transalkylation agents with two or more alkyl groups per aryl group will decrease the molar ratio of aryl groups per alkyl group if the ratio is greater than 0.5, and so on for transalkylation agents with more alkyl groups per aryl group. Third, the transalkylation agent preferably should not adversely affect the yield of the desired monoalkylated aromatic. For example in the context of ethylbenzene production, toluene and cumene are not preferred, because ethylene can alkylate toluene or cumene and produce byproducts that cannot be converted readily to ethylbenzene by alkylation or transalkylation. Even though generally present in the alkylation effluent, ethylbenzene is also not preferred, because ethylbenzene can shift the equilibrium of the reactions away from the formation of ethylbenzene and because ethylbenzene can react with ethylene to produce styrene and ultimately 1,1-DPE. Thus, it would be preferred to not recycle to the alkylation reaction zone a stream containing more than 75 wt-% of the desired monoalkylated aromatic, such as the ethylbenzene or cumene product stream produced by the ethylbenzene or cumene column of the product separation zone. Fourth, the transalkylation agent preferably should not adversely affect the purity of the product stream containing the desired monoalkylated aromatic. For example in the context of ethylbenzene production, xylenes are not preferred because they are relatively difficult to separate from ethylbenzene by distillation. Another reason that xylenes are not preferred is that they can adversely affect ethylbenzene yield by alkylating with ethylene.

In general, the transalkylation agent, when present, is preferably a compound that corresponds to the alkylation substrate alkylated with at least one more alkyl group corresponding to the alkylation agent than the number of alkyl groups on the desired product of alkylating the alkylation substrate with the alkylating agent. In the general case, the transalkylation agent, when present, is different from the desired product of alkylating the alkylation substrate with the alkylation agent. Where the aromatic is benzene and the olefin is ethylene, the transalkylation agent can generally be a polyethylbenzene, and suitable transalkylation agents include di-, tri-, and tetra-ethyl aromatic hydrocarbons such as diethylbenzene, triethylbenzene, diethylmethylbenzene, diethylpropylbenzene, etc. Diethylbenzenes are preferred. Where the aromatic is benzene and the olefin is propylene, the transalkylation agent can generally be a polypropylbenzene, and suitable transalkylation agents include di-, tri-, and tetra-propyl aromatic hydrocarbons such as diisopropylbenzene, triisopropylbenzene, diisopropylmethylbenzene, triisopropylmethylbenzene, etc. Diisopropylbenzenes are especially preferred transalkylation agents.

In practicing the process disclosed herein, the ratio of the weight of the recycled portion of the effluent stream entering the alkylation catalyst bed per unit time to the sum of the weights entering the alkylation catalyst bed of the feed aromatic and the feed olefin per the unit time may be at least 0.1, at least 1.0, at least 2.5, at least 4.0, at least 7.0, or at least 10.0. This ratio is sometimes referred to herein as the effluent recycle ratio or R/FF.

As used herein, aromatic feedstock entering or passing to the alkylation catalyst bed means all of the feed aromatic entering or passing to the alkylation catalyst bed in streams other than an aliquot portion of the effluent stream that enters or passes to the alkylation catalyst bed. As used herein, olefinic feedstock entering or passing to the alkylation catalyst bed means all of the feed olefin entering or passing to the alkylation catalyst bed in streams other than the portion of the effluent stream that enters or passes to the alkylation catalyst bed.

Streams that enter or pass to the alkylation catalyst bed, but which are not an aliquot portion of the effluent stream include but are not limited to the aromatic feed stream, olefinic feed stream, and any other feed stream to the alkylation catalyst bed. Such streams also include streams that have a substantially different composition from the effluent stream but which are produced by separating the effluent stream. For example, a portion of the alkylation effluent stream is typically passed to a separation zone or a product recovery zone to recover monoalkylated aromatic from that portion of the effluent stream. As a result of this separation, one or more streams that have a composition substantially different from the alkylation effluent stream are recovered. These recovered streams include the product monoalkylated aromatic stream, a stream comprising light ends, a recycle stream comprising the feed aromatic, one or more streams comprising polyalkyl aromatics (e.g., dialkyl aromatics and trialkyl aromatics), and a stream comprising heavies.

Of these recovered streams, it is most common for some or all of the feed aromatic recycle stream to be passed to the alkylation catalyst bed. However, some or all of the other recovered streams may also be passed to the alkylation catalyst bed. Any feed aromatic thus passed to the alkylation catalyst bed in some or all of these recovered streams is deemed to be included in the aromatic feedstock entering or passing to the alkylation catalyst bed for purposes of the process disclosed herein. Likewise, any feed olefin passed to the alkylation catalyst bed in some or all of these recovered streams is included in the olefinic feedstock for purposes of the invention. However, any feed aromatic or feed olefin in the aliquot portion of the alkylation catalyst bed effluent that is passed to the alkylation catalyst bed is not counted as aromatic feedstock or olefinic feedstock, respectively, passing to or entering the alkylation catalyst bed, for purposes of the process disclosed herein.

In practicing some embodiments of the process disclosed herein, the ratio of the weight of the olefinic feedstock entering the alkylation catalyst bed per unit time to the sum of the weights of compounds entering the alkylation catalyst bed per the same unit time, multiplied by 100, is generally at most 17 wt-%, at most 10 wt-%, at most 7 wt-%, at most 5 wt-%, or at most 3 wt-%. This ratio is sometimes referred to herein as the feed olefin ratio. The alkylation conditions comprise a maximum feed olefin concentration based on the weight of the feed aromatic, the $C_2$-$C_4$ olefin, and an alkylated derivative of the feed aromatic having from one to six more $C_2$-$C_4$ alkyl groups than the feed aromatic entering the alkylation catalyst bed of at most 17 wt-%, at most 10 wt-%, at most 7 wt-%, at most 5 wt-%, or at most 3 wt-%.

The aromatic feed stream, the olefinic feed stream, and the aliquot portion of the effluent stream are preferably combined upstream of the alkylation catalyst bed to form a combined feed stream having preferably a homogeneous mixture and a uniform composition. If one or more other streams, besides the aromatic feed stream, the olefinic feed stream, and the aliquot portion of the effluent stream, also pass to the alkylation catalyst bed reaction zone, then preferably the other stream or streams mix with the aromatic feed stream, the olefinic feed stream, and the aliquot portion of the effluent stream so that the combined feed steam is formed from all entering streams. This helps to ensure that the feed olefin ratio and/or the maximum feed olefin concentration at alkylation conditions are minimized. The combined stream preferably also has a uniform temperature. Although the feed streams and the aliquot portion of the effluent stream and any other stream, if any, may combine batch-wise or on a non-continuous basis, preferably this combining occurs on a continuous basis. Given the wide range of flow rates and flowing conditions that are permissible for the feed streams and the aliquot portion of the effluent stream and any other stream, if any, and for the alkylation zone when practicing the process disclosed herein, it is not practical to describe herein all of the possible equipment and methods that can be used to combine the streams. However, persons of ordinary skill in the art of fluid mixing are capable of providing the necessary equipment and methods to bring about uniformity of concentration and intimate contact of multiple streams, even if some of the streams are of different phases, e.g., liquid phase, gas phase, mixed phase, or at supercritical conditions. Preferably, the combining occurs in either a pipeline or a vessel geometry at turbulent flow conditions. A brief introduction and references for further information on mixing of fluids can be found at pages 6-34 to 6-36 of Perry's Chemical Engineers' Handbook, Seventh Edition, edited by R. H. Perry, D. W. Green, and J. O. Maloney; McGraw-Hill, New York, 1997.

The alkylation reaction zone can comprise one or more alkylation catalyst beds and/or one or more alkylation catalyst reactors, and each reactor may contain one or more alkylation catalyst beds. Vessels or enclosures that can function as suitable reactors are known to persons of ordinary skill in the art of hydrocarbon processing. A common configuration of an alkylation zone employs two alkylation reactors, each of which has two alkylation catalyst beds. The number of reactors is generally less than eight, and the number of catalyst beds in a given reactor is generally less than six.

Alkylation conditions for the process disclosed herein include a molar ratio of aryl groups per alkyl group of generally from 25 to about 1. The molar ratio may be less than 1, and it is believed that the molar ratio may be 0.75 or lower. The molar ratio of aryl groups per ethyl group (or per propyl group, in cumene production) is preferably at least 1.2. The molar ratio is preferably at most 6, and more preferably at most 3.

In general, for a given molar ratio of alkylation substrate per alkylation agent, especially an olefinic alkylation agent, the greater the molar ratio of aryl groups to alkyl groups in the feed stream, the less is the rise in temperature in the reaction zone that occurs as a result of the alkylation reactions. The alkylation reactions are considered to be moderately exothermic. Although the reactor may have indirect heat exchange means to remove the heat as it is produced, the reactor is preferably adiabatic, and so the outlet temperature of the effluent stream is higher than the inlet temperature of the reactants. An increase in R/FF, as well as an increase in the molar ratio of aryl groups to alkyl groups in the feed stream, increases the quantity of aryl groups available to act as a heat sink in the reaction zone and thus decreases the temperature rise in the reaction zone. While in practicing the process disclosed herein, the appropriate reaction temperature may be generally from 60° C. (140° F.) to the critical temperature of the alkylation substrate, which may be 475° C. (887° F.) or even higher, the inlet temperature in the reaction zone is generally from 60 to 260° C. (140 to 500° F.), and preferably from 100 to 250° C. (212 to 482° F.). Although the temperature rise that occurs in the reaction zone could be from 10 to 190° C. (18 to 342° F.) depending on the total mass flows in the reactor, the temperature rise is generally from 5 to 60° C. (9 to 108° F.), and preferably from 5 to 50° C. (9 to 90° F.).

As described previously, the temperature rise in the reaction zone may be controlled by adjusting the molar ratio of aryl groups to alkyl groups in the feed stream. Minimizing the temperature rise helps prevent high reactor outlet temperatures, which cause undesirable side reactions such as cracking of hydrocarbons to occur. High reaction temperatures can also cause vaporization of benzene and the desired monoalkylaromatic (e.g. ethylbenzene or cumene) in the reaction zone. In one embodiment of the process disclosed herein, the temperature rise in the reaction zone can be controlled by withdrawing an effluent stream from the reaction zone, cooling a portion of the effluent stream, and recycling the cooled portion of the effluent stream to the reaction zone. Although recycling reactor effluent to the reaction zone in this manner may be disadvantageous for some reaction zones, it is not disadvantageous for the process disclosed herein because recycling reactor effluent to the reaction zone does not significantly alter the product distribution when the catalyst is UZM-8 zeolite. A significant alteration in the product distribution is a change in the concentration of any of the products in the reactor effluent stream of more than 0.5 wt-%. A significant alteration in the product distribution does not occur because at the reaction conditions UZM-8 zeolite is such an active promoter of the alkylation reaction between benzene and ethylene and of the transalkylation reaction between benzene and diethylbenzene that these reactions proceed to an extent of at least 80% and generally more than 90% of the way to equilibrium. The analogous reactions between benzene and propylene and between benzene and diisopropylbenzene also proceed to these high extents. Thus, recycling reactor effluent to the reaction zone does not interfere in a significant way with the extent of the alkylation or transalkylation reactions, and recycling reactor effluent may be employed for the purpose of controlling reaction zone temperatures.

Alkylation is preferably performed in the liquid phase. Consequently, reaction pressure needs to be sufficiently high to ensure at least a partial liquid phase. Where ethylene is the olefin, the pressure range for the reactions is usually from about 1379 to 6985 kPa(g) (200 to about 1000 psi(g)), more commonly from about 2069 to 4137 kPa(g) (300 to about 600 psi(g)), and even more commonly from about 3103 to 4137 kPa(g) (450 to about 600 psi(g)). Preferably, the reaction conditions are sufficient to maintain benzene in a liquid phase and are supercritical conditions for ethylene. Pressure is not a critical variable in the success of the process disclosed herein, however, and the only criterion is that the pressure be sufficiently great to ensure at least partial liquid phase. For olefins other than ethylene, the process disclosed herein may be practiced generally at a pressure of from 345 to 6985 kPa(g) (50 to 1000 psi(g)).

The weight hourly space velocity (WHSV) of the feed olefin may range from 0.01 to 8.0 $hr^{-1}$. As used herein, weight hourly space velocity of a component means the weight flow rate of the component per hour divided by the catalyst weight, where the weight flow rate of the component per hour and the catalyst weight are in the same weight units. The WHSV of aromatics, including benzene and a polyalkylaromatic having at least two $C_2^+$ groups, if any, is generally from 0.3 to 480 $hr^{-1}$. In a preferred embodiment, in which the polyalkyl aromatic is a diethylbenzene or a triethylbenzene, the molar ratio of benzene per ethylene is from 1.5:1 to 6:1, the WHSV of ethylene is from 0.1 to 6.0 $hr^{-1}$, and the WHSV of aromatics including benzene and the polyethylbenzenes is from 0.5 to 70 $hr^{-1}$.

In the context of ethylbenzene production, the principal reaction that occurs in the reaction zone is the alkylation of the benzene by ethylene to produce ethylbenzene. In addition, other reactions can occur in the reaction zone. For example, benzene can transalkylate with a polyethylbenzene to produce ethylbenzene. Also, polyethylbenzene can be alkylated with ethylene. The reactor effluent stream thus contains ethylbenzene and may also contain unreacted polyethylbenzene or a byproduct of an alkylation side reaction involving the polyethylbenzene or a byproduct of a transalkylation side reaction involving the polyethylbenzene. Although the extent to which other reactions form byproducts is diminished by the practice of the process disclosed herein, the reactor effluent stream usually contains the byproducts of these side reactions. The reactor effluent stream may also contain unreacted benzene, as well as a byproduct of an alkylation side reaction involving benzene or a byproduct of a transalkylation side reaction involving benzene. In addition, the reactor effluent stream may contain unreacted ethylene, but the concentration of unreacted ethylene is likely to be insignificant because benzene is usually present at least in a stoichiometric proportion. Although it is not common for the feed stream to contain $C_1$ to $C_3$ paraffins in addition to ethylene, if ethane is present in the feed stream then the reactor effluent stream may also contain unreacted ethane.

The alkylation effluent stream contains preferably less than 1.0 wt-% diarylalkane, more preferably less than 0.5 wt-% diarylalkane, and even more preferably less than 0.2 wt-% diarylalkane, relative to the monoalkylated aromatic. These low yields of diarylalkane relative to the monoalkylated aromatic can be attained using an alkylation catalyst bed without using a separate transalkylation catalyst bed that is distinct from the alkylation catalyst bed.

In practicing the process disclosed herein, the reactor effluent stream is separated into at least two aliquot portions, in order that an aliquot portion can be recycled and passed to the alkylation reaction zone. Persons of ordinary skill in the art of fluid mechanics are capable of providing the necessary equipment and methods, including control methods, to ensure that the alkylation effluent is a uniform stream and that the portion separated from the reactor effluent and recycled to the alkylation reaction zone is an aliquot portion. For further information on distributing fluids and on controlling fluid flow, refer to pages 6-32 to 6-36 and to Section 8 of Perry's Chemical Engineers' Handbook, Seventh Edition.

When one aliquot portion of the alkylation effluent is recycled to and introduced into the alkylation reaction zone, at least one other aliquot portion of the alkylation effluent generally passes to a separation zone for recovering the monoalkylated aromatic. The separation zone generally comprises a benzene fractionation column in order to recycle unreacted benzene to the alkylation zone, and an ethylbenzene fractionation column in order to recover ethylbenzene as product from the heavier polyalkylbenzenes. A polyalkylbenzene fractionation column may also be used in order to separate diethylbenzenes and triethylbenzenes from the other heavier polyalkylbenzenes, particularly where the polyalkylbenzene that is present in the feed stream is a diethylbenzene or a triethylbenzene. The separation zone generally does not comprise a deethanizer unless the concentrations of unreacted ethylene, ethane, or light $C_3$-minus paraffins in the reactor effluent are high enough to justify their being separated from the reactor effluent stream.

Thus, in addition to producing a fraction comprising the monoalkylated aromatic, the separation zone may also produce one or more other fractions of the alkylation effluent from the aliquot portion of the alkylation effluent. Accordingly, in addition to recycling an aliquot portion of the alkylation effluent to the alkylation reaction zone, some or all of at least one of these other fractions recovered from the separation zone can also pass to the alkylation reaction zone. These other recovered fractions can comprise polyethylbenzenes, which in turn can be recycled to the alkylation reaction zone as transalkylation agents. In a commercial ethylbenzene process, several process streams produced by the separation zone can be used to supply such polyethylbenzenes to the alkylation reaction zone. Hereinafter described FIGS. 1, 2, and 3 identify several such process streams.

The catalyst for the process disclosed herein contains one or more members of the family of aluminosilicate and substituted aluminosilicate zeolites designated UZM-8. U.S. Pat. No. 6,756,030 B1, incorporated herein by reference, describes UZM-8 and its preparation, and therefore it is not necessary herein to describe these in detail. Briefly, UZM-8 zeolites are prepared in an alkali-free reaction medium in which only one or more organoammonium species are used as structure directing agents. In this case, the microporous crystalline zeolite (UZM-8) has a composition in the as-synthesized form and on an anhydrous basis expressed by the empirical formula:

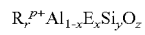

where R is at least one organoammonium cation selected from the group consisting of protonated amines, protonated diamines, quaternary ammonium ions, diquaternary ammonium ions, protonated alkanolamines and quaternized alkanolammonium ions. Preferred organoammonium cations are those that are non-cyclic or those that do not contain a cyclic group as one substituent. Of these those that contain at least two methyl groups as substituents are especially preferred. Examples of preferred cations include without limitation DEDMA, ETMA, HM and mixtures thereof. The ratio of R to (Al+E) is represented by "r" which varies from about 0.05 to about 5. The value of "p" which is the weighted average valence of R varies from 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation $$z=(r \cdot p+3+4 \cdot y)/2.$$

The UZM-8 zeolites can be prepared using both organoammonium cations and alkali and/or alkaline earth cations as structure directing agents. As in the alkali-free case above, the same organoammonium cations can be used here. Alkali or alkaline earth cations are observed to speed up the crystallization of UZM-8, often when present in amounts less than 0.05 M+/Si. For the alkali and/or alkaline earth metal containing systems, the microporous crystalline zeolite (UZM-8) has a composition in the as-synthesized form and on an anhydrous basis expressed by the empirical formula:

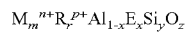

where M is at least one exchangeable cation and is selected from the group consisting of alkali and alkaline earth metals. Specific examples of the M cations include but are not limited to lithium, sodium, potassium, rubidium, cesium, calcium, strontium, barium and mixtures thereof. Preferred R cations include without limitation DEDMA, ETMA, HM and mixtures thereof. The value of "m" which is the ratio of M to (Al+E) varies from about 0.01 to about 2. The value of "n" which is the weighted average valence of M varies from about 1 to about 2. The ratio of R to (Al+E) is represented by "r" which varies from 0.05 to about 5. The value of "p" which is the weighted average valence of R varies from about 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation $$z=(m \cdot n+r \cdot p+3+4 \cdot y)/2$$

where M is only one metal, then the weighted average valence is the valence of that one metal, i.e. +1 or +2. However, when more than one M metal is present, the total amount of

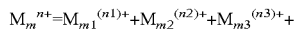

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

Similarly when only one R organic cation is present, the weighted average valence is the valence of the single R cation, i.e., +1 or +2. When more than one R cation is present, the total amount of R is given by the equation.

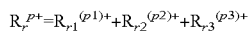

and the weighted average valence "p" is given by the equation $$p = \frac{p_1 \cdot r_1 + p_2 \cdot r_2 + p_3 \cdot r_3 + \ldots}{r_1 + r_2 + r_3 + \ldots}$$

The microporous crystalline zeolites used in the process disclosed herein are prepared by a hydrothermal crystallization of a reaction mixture prepared by combining reactive sources of R, aluminum, silicon and optionally M and E. The sources of aluminum include but are not limited to aluminum alkoxides, precipitated aluminas, aluminum metal, sodium aluminate, organoammonium aluminates, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica, alkali silicates and organoammonium silicates. A special reagent consisting of an organoammonium aluminosilicate solution can also serve as the simultaneous source of Al, Si, and R. Sources of the E elements include but are not limited to alkali borates, boric acid, precipitated gallium oxyhydroxide, gallium sulfate, ferric sulfate, ferric chloride, chromium nitrate and indium chloride. Sources of the M metals include the halide salts, nitrate salts, acetate salts, and hydroxides of the respective alkali or alkaline earth metals. R can be introduced as an organoammonium cation or an amine. When R is a quaternary ammonium cation or a quaternized alkanolammonium cation, the sources include but are not limited the hydroxide, chloride, bromide, iodide and fluoride compounds. Specific examples include without limitation DEDMA hydroxide, ETMA hydroxide, tetramethylammonium hydroxide, tetraethylammonium hydroxide, hexamethonium bromide, tetrapropylammonium hydroxide, methyltriethylammonium hydroxide, tetramethylammonium chloride and choline chloride. R may also be introduced as an amine, diamine, or alkanolamine that subsequently hydrolyzes to form an organoammonium cation. Specific non-limiting examples are N,N,N',N'-tetramethyl-1,6-hexanediamine, triethylamine, and triethanolamine. Preferred sources of R without limitation are ETMAOH, DEDMAOH, and hexamethonium dihydroxide (HM(OH)$_2$).

The reaction mixture containing reactive sources of the desired components can be described in terms of molar ratios of the oxides by the formula:

where "a" varies from 0 to about 25, "b" varies from about 1.5 to about 80, "c" varies from 0 to 1.0, "d" varies from about 10 to about 100, and "e" varies from about 100 to about 15000. If alkoxides are used, it is preferred to include a distillation or evaporative step to remove the alcohol hydrolysis products. The reaction mixture is now reacted at a temperature of about 85° C. to about 225° C. (185 to 437° F.) and preferably from about 125° C. to about 150° C. (257 to 302° F.) for a period of about 1 day to about 28 days and preferably for a time of about 5 days to about 14 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. (212° F.).

The UZM-8 aluminosilicate zeolite, which is obtained from the above-described process, is characterized by an x-ray diffraction pattern, having at least the d-spacings and relative intensities set forth in Table A below

TABLE A d-Spacings and Relative Intensities for as-synthesized UZM-8

| 2-θ | d(Å) | I/I$_0$ % |
|---|---|---|
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs |

The UZM-8 compositions are stable to at least 600° C. (1112° F.) (and usually at least 700° C. (1292° F.)). The characteristic diffraction lines associated with typical calcined UZM-8 samples are shown below in table B. The as-synthesized form of UZM-8 is expandable with organic cations, indicating a layered structure.

TABLE B d-Spacings and Relative Intensity for Calcined UZM-8

| 2-θ | d(Å) | I/I$_0$ % |
|---|---|---|
| 4.05-4.60 | 21.80-19.19 | w-m |
| 7.00-7.55 | 12.62-11.70 | m-vs |
| 8.55-9.15 | 10.33-9.66 | w-vs |
| 12.55-13.15 | 7.05-6.73 | w |
| 14.30-14.90 | 6.19-5.94 | m-vs |
| 19.55-20.35 | 4.54-4.36 | w-m |
| 22.35-23.10 | 3.97-3.85 | m-vs |
| 24.95-25.85 | 3.57-3.44 | w-m |
| 25.95-26.75 | 3.43-3.33 | m-s |

An aspect of the UZM-8 synthesis that contributes to some of its unique properties is that it can be synthesized from a homogenous solution. In this chemistry, soluble aluminosilicate precursors condense during digestion to form extremely small crystallites that have a great deal of external surface area and short diffusion paths within the pores of the crystallites. This can affect both adsorption and catalytic properties of the material.

As-synthesized, the UZM-8 material will contain some of the charge balancing cations in its pores. In the case of syntheses from alkali or alkaline earth metal-containing reaction mixtures, some of these cations may be exchangeable cations that can be exchanged for other cations. In the case of organoammonium cations, they can be removed by heating under controlled conditions. In the cases where UZM-8 is prepared in an alkali-free system, the organoammonium cations are best removed by controlled calcination, thus generating the acid form of the zeolite without any intervening ion-exchange steps. The controlled calcination conditions include the calcination conditions described herein below for the composite catalyst, and it may sometimes be possible desirable to perform the controlled calcination of the zeolite after the zeolite has been combined with a binder. On the other hand, it may sometimes be possible to remove a portion of the organoammonium via ion exchange. In a special case of ion exchange, the ammonium form of UZM-8 may be generated via calcination of the organoammonium form of UZM-8 in an ammonia atmosphere.

The catalyst used in the process disclosed herein preferably contains calcined UZM-8. Calcination of as-synthesized UZM-8 effects changes such as in the x-ray diffraction pattern. The UZM-8 zeolite used in the catalyst used in the process disclosed herein contains preferably less than 0.1 wt-%, more preferably less than 0.05 wt-%, and even more preferably less than 0.02 wt-% of alkali and alkaline earth metals.

For use in the process disclosed herein, the zeolite preferably is mixed with a binder for convenient formation of catalyst particles in a proportion of about 5 to 100 mass % zeolite and 0 to 95 mass-% binder, with the zeolite preferably comprising from about 10 to 90 mass-% of the composite. The binder should preferably be porous, have a surface area of about 5 to about 800 m$^2$/g, and be relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, etc.; silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314, which is hereby incorporated herein by reference in its entirety. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50-200° C. (122-392° F.) and subjected to a calcination procedure at a temperature of about 450-700° C. (842-1292° F.) for a period of about 1 to about 20 hours. This treatment effects conversion of the hydrogel to the corresponding alumina matrix.

The catalyst composite is dried at a temperature of from about 100° to about 320° C. (212 to 608° F.) for a period of from about 2 to about 24 or more hours and, usually, calcined at a temperature of from about 400° to about 650° C. (752 to 1202° F.) in an air atmosphere for a period of from about 1 to about 20 hours. The calcining in air may be preceded by heating the catalyst composite in nitrogen to the temperature range for calcination and holding the catalyst composite in that temperature range for from about 1 to about 10 hours. A catalyst composite used in the process disclosed herein preferably has an x-ray diffraction pattern having at least the d-spacings and relative intensities set forth in Table B.

The binder used in the catalyst composite for the process disclosed herein preferably contains less alkali and alkaline earth metals than the UZM-8 zeolite used in the catalyst composite, and more preferably contains little or no alkali and alkaline earth metals. Therefore, the catalyst composite has a content of alkali and alkaline earth metals of less than that of the UZM-8 zeolite used in forming the catalyst composite, owing to the binder effectively lowering the alkali and alkaline earth metals content of the catalyst composite as a whole.

FIGS. 1-8 illustrate embodiments of the process disclosed herein. For clarity and simplicity, some items associated with the operation of the process have not been shown. These items include flow and pressure control valves, pumps, heat exchangers, temperature and pressure monitoring systems, reactor and fractionator internals, etc., which may be of customary design. Such representation of these embodiments is not intended to limit the scope of the present invention as set forth in the claims.

In the description of FIGS. 1-8 that follows, the reactors in FIGS. 1-8 are referred to as alkylation reactors except for reactor 630 in FIG. 6, which is referred to as a transalkylation reactor. Although alkylation reactions take place in the alkylation reactors in FIGS. 1-8, it should be noted that transalkylation reactions may also take place in the alkylation reactors in FIGS. 1-8, depending on the conditions and catalyst in the reactors. It is believed, however, that the occurrence of transalkylation reactions in the alkylation reactors in FIGS. 1-8 is not a requirement of the process disclosed herein, since the process disclosed herein is a process that operates at a high effluent recycle ratio, whether or not transalkylation reactions occur therein. Referring to reactors in FIGS. 1-8 as alkylation reactors also is not intended to exclude transalkylation reactions from occurring in such alkylation reactors.

Referring now to FIG. 1, FIG. 1 illustrates an embodiment of the process disclosed herein in which not only an aliquot portion of the alkylation effluent but also a polyethylbenzene column overhead stream is recycled to the alkylation reactor. The overhead stream of the polyethylbenzene column typically contains only diethylbenzenes and triethylbenzenes, contains a relatively low concentration of ethylbenzene, and does not contain a high concentration of the heaviest polyethylbenzenes that are produced in the alkylation reactors. In FIG. 1, a stream comprising ethylene enters the process in line 14 and is admixed with a stream flowing through line 15 that comprises benzene, diethylbenzenes, triethylbenzenes, and tetraethylbenzenes, and which has, in addition, been formed in part from a recycled aliquot portion of the second alkylation reactor effluent stream via lines 36 and 46. This admixing produces a first alkylation reactor feed stream carried by line 16. The benzene that is present in the stream flowing through line 15 is benzene that has been added as make-up to the process and benzene that has been recycled within the process. Make-up benzene can enter the process in line 10, admix with a stream flowing through line 12, and flow into line 15. Recycle benzene flows from benzene column 40 and through line 44, and admixes with the aliquot portion of the second alkylation reactor effluent stream flowing in line 36 to form the stream flowing through line 46. The stream in line 46 admixes with a recycled polyethylbenzene column overhead stream flowing in line 68 to form the stream that flows through line 12, which flows into line 15. The recycle polyalkylbenzenes flowing in line 15 comprise diethylbenzenes, triethylbenzenes, and optionally tetraethylbenzenes from the polyethylbenzene column overhead stream. The components of the second alkylation reactor effluent stream include polyethylbenzenes, such as not only byproducts of the alkylation of benzene with ethylene but also byproducts of the alkylation and transalkylation of various components of the second alkylation reactor effluent stream. Thus, the first alkylation reactor feed steam flowing through line 16 contains ethylene, benzene, diethylbenzenes, triethylbenzenes, tetraethylbenzenes, and components of the second alkylation reactor effluent stream. The first reactor feed stream flowing through line 16 may be heated in a heat exchanger or a heater, which is not shown, and enters first alkylation reactor 20. The first reactor feed stream contacts a UZM-8 zeolite catalyst maintained at reaction conditions to form ethylbenzene by alkylating benzene with at least a portion of the ethylene. The reaction conditions may also be sufficient to form ethylbenzene by transalkylating benzene with at least a portion of the diethylbenzenes, triethylbenzenes, or tetraethylbenzenes. The first alkylation reactor effluent stream comprises benzene, ethylbenzene, byproducts of the alkylation of benzene with ethylene, and byproducts of the alkylation and transalkylation of diethylbenzenes, triethylbenzenes, and tetraethylbenzenes in the first reactor feed stream. Typically, the byproducts in the first reactor effluent stream comprise diethylbenzenes, triethylbenzenes, tetraethylbenzenes, butylbenzenes, dibutyl-benzenes, tributylbenzenes, ethylbutylbenzenes, diethylbutylbenzenes, and diphenylethane.

The first alkylation reactor effluent stream exits first reactor 20 in line 18 and enters heat exchanger 22, where the first reactor effluent stream is cooled by exchanging heat indirectly with boiler feed water to produce low pressure steam. The cooled first reactor effluent stream passes through line 24 and is admixed with ethylene that enters the process in line 26. This produces a second alkylation reactor feed stream carried by line 28. The second alkylation reactor feed stream may be heated in a heat exchanger or a heater, which is not shown, and enters second alkylation reactor 30. The second reactor feed stream contacts a UZM-8 zeolite catalyst to alkylate benzene with ethylene in order to produce ethylbenzene. Additional ethylbenzene may be produced in second alkylation reactor 30 by the transalkylation of benzene with diethylbenzenes, triethylbenzenes, and tetraethylbenzenes. The second alkylation reactor effluent stream can include not only byproducts of the alkylation of benzene with ethylene and of the transalkylation of benzene with diethylbenzenes, triethylbenzenes, and tetraethylbenzenes but also byproducts of the alkylation and transalkylation of components of the first alkylation reactor effluent stream. Typically, the byproducts in the second reactor effluent stream comprise those byproducts listed previously as being in the first reactor effluent stream. The second reactor effluent stream exits second alkylation reactor 30 in line 32. The second reactor effluent stream then divides into two aliquot portions, one of which is recycled to first alkylation reactor 20. This recycled aliquot portion of the second alkylation reactor effluent stream may, while flowing through line 36, be cooled in a heat exchanger or a cooler, which is not shown. The second aliquot portion of the alkylation reactor effluent stream flows through line 34 and may be depressured by passing through a pressure control valve which is not shown, may be heated in a heater or heat exchanger which is also not shown, or both. The second aliquot portion of the second alkylation reactor effluent then enters benzene column 40.

Benzene column 40 separates the second alkylation reactor effluent stream by distillation into two streams. A benzene column overhead steam comprising benzene exits the benzene column through line 44 and is recycled to first alkylation reactor 20. A benzene column bottom stream comprising the product ethylbenzene and the byproducts including polyethylbenzenes exits the benzene column in line 42 and enters ethylbenzene column 50.

Ethylbenzene column 50 separates the benzene column bottom stream by distillation into two streams. An ethylbenzene column overhead stream comprising the product ethylbenzene exits ethylbenzene column 50 in line 52 and is recovered from the process. An ethylbenzene column bottom stream comprises byproduct ethylbenzenes, typically including diethylbenzenes, triethylbenzenes, tetraethylbenzenes, butylbenzenes, dibutylbenzenes, tributylbenzenes, ethylbutylbenzenes, and diethylbutylbenzenes, and diphenylethane. The ethylbenzene column bottom stream exits ethylbenzene column 50 in line 54, and passes to polyethylbenzene column 60.

Polyethylbenzene column 60 separates the ethylbenzene column bottom steam into two streams. A polyethylbenzene column bottom stream comprising polyethylbenzenes heavier than triethylbenzene or tetraethylbenzene exits from the bottom of polyethylbenzene column 60 in line 82 and is rejected from the process. The polyethylbenzene column overhead steam comprising diethylbenzenes, triethylbenzenes, and optionally tetraethylbenzenes exits polyethylbenzene column 60 in line 68 and recycles to first alkylation reactor 20.

Figure 2:
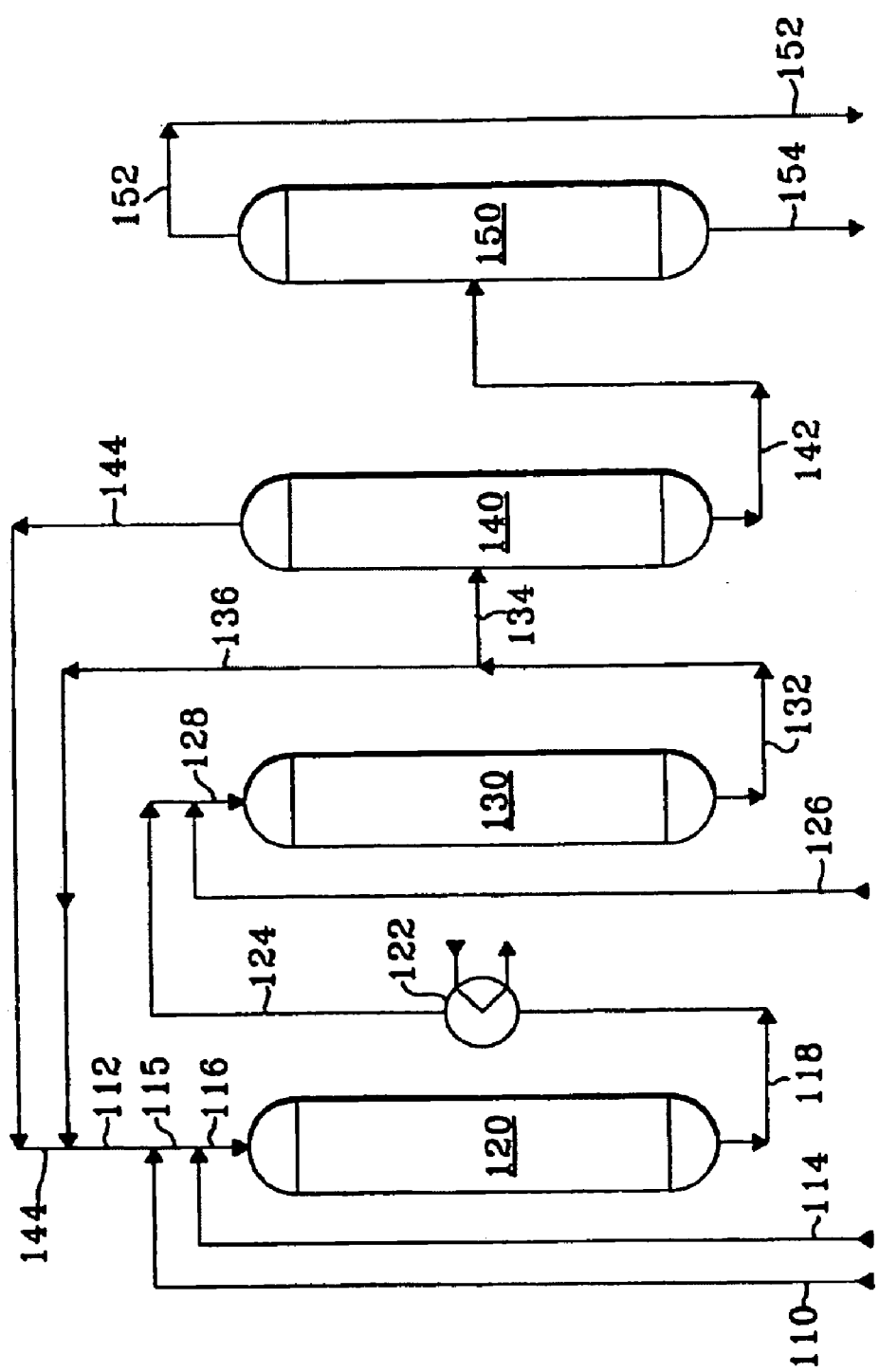

FIG. 2 illustrates another embodiment of the process disclosed herein in which an aliquot portion of the second alkylation reactor effluent stream is recycled to the first alkylation reactor. At least in theory, the aliquot portion of the second alkylation reactor effluent stream can be recycled at a rate that is limited only by economic considerations. Except for the aliquot portion of the alkylation reactor effluent stream that is passed downstream to product separation facilities, the second alkylation reactor effluent stream is available for recycle in what amounts to an unlimited quantity. Unlike other streams in the process, the second alkylation reactor effluent stream can be recycled to the alkylation reactors without interfering with the extent to which the alkylation and transalkylation reactions proceed.

Referring now to FIG. 2, a make-up stream containing propylene and propane enters the process in line 114 and combines with a stream flowing through line 115 that is formed from make-up benzene from line 110, recycle benzene from benzene column 140 via lines 144 and 112, and a recycled aliquot portion of the second alkylation reactor effluent stream via lines 136 and 112. Thus, the stream flowing through line 115 carries at least one recycle polyalkylbenzene comprising at least two $C_3$ groups, such as dipropylbenzene, tripropylbenzene, and heavier polyalkylbenzenes. Whether any or all of these recycle polyalkylbenzenes is in fact present in the stream in line 115 depends on which of these recycle polyalkylbenzenes is present in the aliquot portion of the second alkylation reactor effluent stream that is recycled through line 136. Accordingly, in this embodiment the first alkylation reactor feed stream flowing through line 116 contains propylene, propane, benzene, and components of the second alkylation reactor effluent stream, including polyisopropylbenzenes. Polypropylbenzenes in the second alkylation reactor effluent stream can include not only byproducts of the alkylation of benzene with propylene but also byproducts of the alkylation and transalkylation of various components of the second alkylation reactor effluent stream. The first alkylation reactor feed stream flows through line 116 and enters first alkylation reactor 120, which contains a UZM-8 zeolite catalyst. The first alkylation reactor effluent stream contains cumene and other components and exits first alkylation reactor 120 in line 118, is cooled in heat exchanger 122, passes through line 124, and combines with a make-up stream containing propylene and propane from line 126 to produce the second alkylation reactor feed stream. The second alkylation reactor feed stream flows through line 128 and enters second alkylation reactor 130, which contains a UZM-8 zeolite catalyst. The second alkylation reactor effluent stream contains cumene and other components and exits second alkylation reactor 130 in line 132. An aliquot portion of the second alkylation reactor effluent stream is cooled in a heat exchanger or a cooler, which is not shown, and is recycled to first alkylation reactor 120 through lines 136, 112, 115, and 116. Another aliquot portion of the second alkylation reactor effluent stream passes through line 134. This other aliquot portion of the second alkylation reactor effluent stream may be depressured, heated, depropanized in a depropanizer that is not shown, or subject to any combination of these three treatments. The resulting stream then enters benzene column 140. As an alternative, prior to combining with the stream in line 112 the make-up benzene contained in line 110 may be processed in the depropanizer column if it exists to remove excess water contained in the make-up benzene and produce a drier benzene stream for processing in the first alkylation reactor 120.

Benzene column 140 separates components in the second reactor effluent stream into a benzene column overhead stream comprising benzene that is recycled to first alkylation reactor 120 via line 144 and into a benzene column bottom stream comprising cumene and byproduct polypropylbenzenes that flows through line 142 to cumene column 150. Cumene column 150 separates the benzene column bottom stream into a cumene column overhead stream comprising cumene that is recovered from the process through line 152 and into a cumene column bottom stream comprising byproducts such as dipropylbenzenes, tripropylbenzenes, hexylbenzenes, dihexylbenzenes, trihexylbenzenes, propylhexylbenzenes, dipropylhexylbenzenes, and diphenylpropane. The cumene column bottom stream flows through line 154. To produce additional cumene, polypropylbenzenes in the cumene column bottom stream may be processed in a transalkylation reactor, which is not shown.

Figure 3:
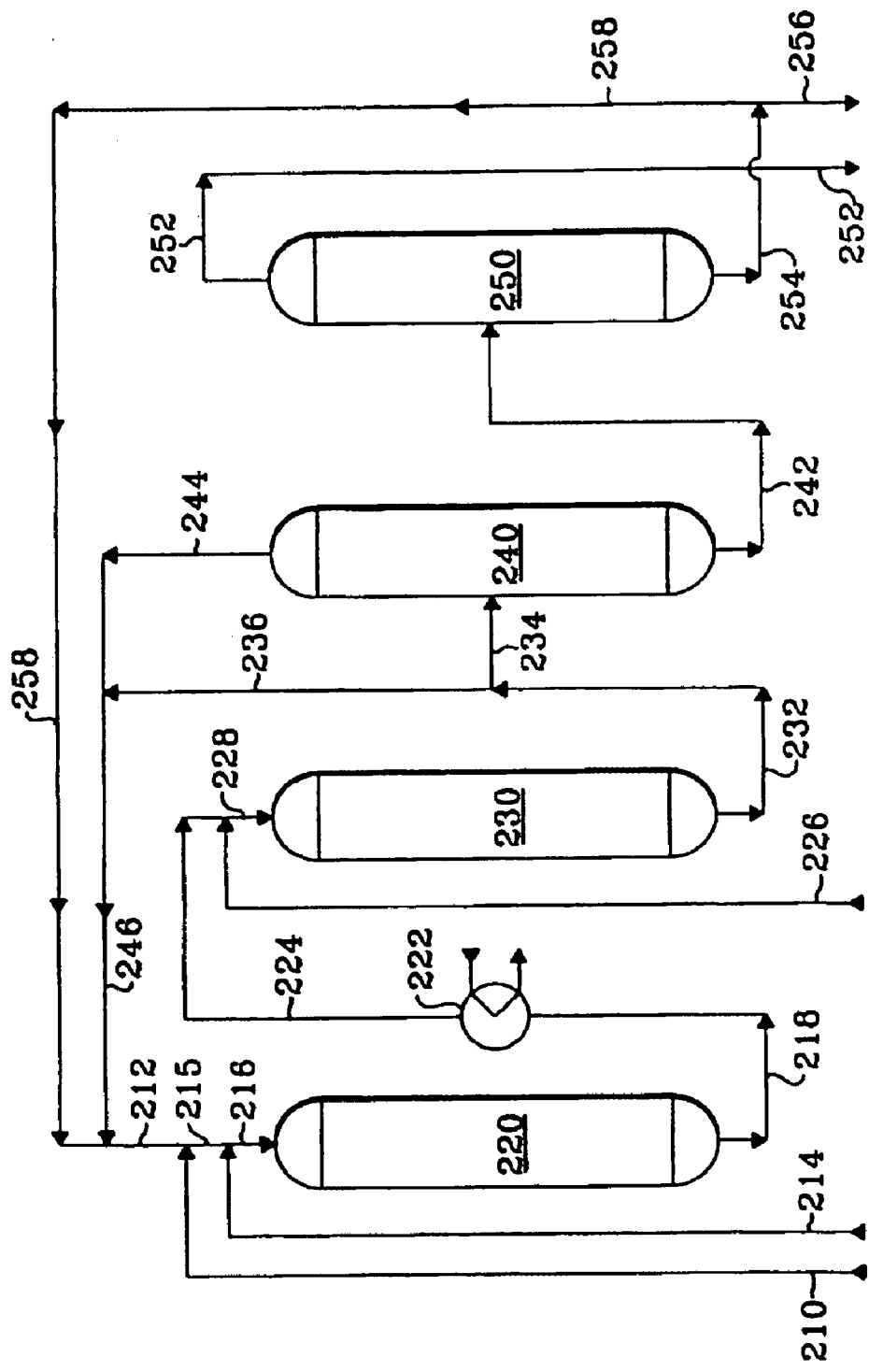

FIG. 3 illustrates another embodiment of the process disclosed herein in which a butylbenzene column bottom stream is recycled along with an aliquot portion of the second alkylation reactor effluent stream to the first reactor. The bottom stream of the butylbenzene column contains a relatively low concentration of butylbenzene. Referring now to FIG. 3, make-up butenes and butane enter the process in line 214 and combine with a stream flowing through line 215 that is formed from a make-up benzene from line 210, a recycled portion of a benzene column overhead steam via lines 244, 246, and 212, a recycled portion of the butylbenzene column bottom stream via lines 254, 258, and 212, and a recycled aliquot portion of the second alkylation reactor effluent stream via lines 236, 246, and 212. Thus, the feed stream in line 216 to first alkylation reactor 220 contains butenes, butane, benzene, and components that are present in the butylbenzene column bottom stream, such as dibutylbenzenes, tributylbenzenes, octylbenzenes, dioctylbenzenes, trioctylbenzenes, butyloctylbenzenes, dibutyloctylbenzenes, and diphenylbutane, as well as any other components of the second alkylation reactor effluent stream. The first alkylation reactor contains a UZM-8 zeolite catalyst. The first alkylation reactor effluent stream containing butylbenzene and other components exits the first alkylation reactor 220 in line 218, is cooled in heat exchanger 222, passes through line 224, and combines with make-up butenes and butane from line 226 to produce the second alkylation reactor feed stream. The second alkylation reactor feed stream flows through line 228 and enters second alkylation reactor 230, which contains a UZM-8 zeolite catalyst. The second alkylation reactor effluent stream exits second alkylation reactor 230 via line 232. The second reactor effluent stream then divides into two aliquot portions, one of which is recycled to the first alkylation reactor 220. This recycled aliquot portion of the second alkylation reactor effluent stream may, while flowing through line 236, be cooled in a heat exchanger or a cooler, which is not shown. The second aliquot portion of the alkylation reactor effluent stream flows through a line 234 and may be depressured, heated, debutanized in a debutanizer column that is not shown, or subject to any combination of these three treatments. The resulting stream then enters benzene column 240. As an alternative, prior to combining with the stream in line 212 the make-up benzene contained in line 210 may be processed in the debutanizer column if it exists to remove excess water contained in the make-up benzene and produce a drier benzene stream for processing in the first alkylation reactor 220.

Benzene column 240 produces the benzene column overhead stream comprising benzene in line 244 which is recycled to the first alkylation reactor 220 and a benzene column bottom stream comprising the product butylbenzene and byproduct alkylbenzenes that flows through line 242 to butylbenzene column 250. A butylbenzene column overhead stream comprising butylbenzene is recovered from the process through line 252. A butylbenzene column bottom stream comprising byproduct alkylbenzenes, such as dibutylbenzenes, tributylbenzenes, octylbenzenes, dioctylbenzenes, trioctylbenzenes, butyloctylbenzenes, and dibutyloctylbenzenes, and diphenylbutane flows through line 254. A portion of the butylbenzene column bottom stream is recycled via line 258 to first alkylation reactor 220. A small part of the butylbenzene column bottoms stream is removed from the process via line 256 in order to provide a purge for heavy polyalkylbenzenes or for further processing of polyalkylbenzenes in a transalkylation zone which is not shown to produce additional butylbenzene.

Other embodiments of the process disclosed herein include the processes shown in FIGS. 1-3 using instead any of the other feed olefins disclosed herein. Other embodiments also include combinations of the processes shown in FIGS. 1-3 using the same feed olefin or other feed olefins disclosed herein. For example, in FIG. 1, a portion of the bottoms stream of the ethylbenzene column 50 can be recycled to the first alkylation reactor 20. The following descriptions of FIGS. 4-8 are written in terms of ethylene as the feed olefin, but any other feed olefin may also be used.

Referring now to FIG. 4, a stream comprising ethylene enters the process in line 404. This stream is admixed with a stream flowing through line 402 that comprises benzene and with a cooled aliquot portion of alkylation reactor effluent flowing through line 422, thereby producing an alkylation reactor feed stream flowing through the line 406 that contains ethylene, benzene, and components of the alkylation reactor effluent. The turbulence that occurs as a result of the combining and admixing of the streams and the flowing of the alkylation reactor feed stream through line 406 makes the concentration of olefin (ethylene) uniform in the alkylation reactor feed stream. The alkylation reactor feed stream flowing through line 406 may be heated in a heat exchanger or heater, which is not shown, and enters alkylation reactor 410. Turbulence within the heat exchanger or heater, if present, may further help to ensure uniform ethylene concentration. The alkylation reactor feed stream contacts bed 412 of solid alkylation catalyst comprising UZM-8 zeolite maintained at reaction conditions to form ethylbenzene by alkylating benzene with at least a portion of the ethylene. The reactor effluent stream exits reactor 410 via line 414, and then divides into two aliquot portions. One aliquot portion passes through line 416 to another alkylation reactor or a product separation zone, which is not shown. The other aliquot portion of the reactor effluent stream flows through line 418, enters heat exchanger 420, where the aliquot portion is cooled by exchanging heat indirectly with boiler feed water to produce low pressure steam, and then flows through line 422 to combine with the streams flowing in lines 402 and 404, as described previously.

Referring now to FIG. 5, ethylene enters via line 524 and combines with a stream flowing through line 526 to form the stream flowing through line 528. The stream in line 526 is formed from benzene in line 576 and an aliquot portion of the recycled and cooled aliquot portion of the second alkylation reactor effluent stream in line 566. Thus, the stream flowing through line 528, which is the first alkylation reactor feed stream, contains ethylene, benzene, and recycled components of the second alkylation reactor effluent stream, which may include recycled polyethylbenzenes, such as diethylbenzenes, triethylbenzenes, and heavier polyethylbenzenes. Turbulent flow and in-line mixers, which are not shown, in line 528 help ensure good mixing and uniformity of the ethylene concentration in the feed stream as it enters first alkylation reactor 530. The first alkylation reactor 530 contains two beds of UZM-8 zeolite catalyst, 532 and 534, and the first alkylation reactor feed stream enters bed 532. An effluent stream exits bed 532 and combines with an ethylene-containing stream flowing through line 536 to form the feed stream for bed 534. The introduction of ethylene between beds 532 and 534 is done in a manner and/or using distribution devices so that the ethylene concentration in the feed stream for bed 534 is uniform. An effluent stream exits bed 534 and first alkylation reactor 530 via line 538, is cooled in heat exchanger 540, passes through line 542, and combines with ethylene from line 544 to produce the stream flowing through line 546. The second alkylation reactor feed stream flowing in line 547 is formed by combining the stream flowing in line 546 with a recycled and cooled aliquot portion of the second alkylation reactor effluent stream in line 545. Turbulence in lines 546 and 547 helps ensure that the ethylene concentration is uniform in the second alkylation reactor feed stream as the stream enters second alkylation reactor 550. The second alkylation reactor 550 contains two beds of UZM-8 zeolite alkylation catalyst, 553 and 555, and the second alkylation reactor feed stream enters bed 553. An effluent stream exits bed 553 and combines with an ethylene-containing stream flowing through line 548 to form the feed stream for bed 555. The introduction of ethylene between beds 553 and 555 is done in a manner so that the concentration of the ethylene in the feed stream to bed 555 is uniform. An effluent stream exits bed 555 and leaves alkylation reactor 550 via line 552. The effluent stream in line 552 divides into two aliquot portions. One aliquot portion flows through line 554 to a downstream alkylation reactor or to a product separation zone, which is not shown. The other aliquot portion of the second alkylation reactor effluent stream flows through line 558, enters heat exchanger 560 where the aliquot portion is cooled, flows through line 562, and then itself divides into two aliquot portions. One aliquot flows to the first alkylation reactor 530 via line 566 and the other aliquot portion flows to the second alkylation reactor 550 via line 545.

Referring now to FIG. 6, a stream comprising polyethylbenzenes, such as diethylbenzenes, triethylbenzenes, and tetraethylbenzenes, enters the process via line 624 and is admixed with a stream flowing through line 676 that comprises benzene thereby producing a transalkylation reactor feed stream flowing through line 628. The transalkylation reactor feed stream in line 628 may be heated in a heat exchanger or heater, which is not shown, and enters transalkylation reactor 630, where the feed stream contacts bed 632 of solid transalkylation catalyst maintained at reaction conditions to form ethylbenzene by transalkylating benzene with at least a portion of the polyethylbenzenes. However, it should be noted that, regarding this embodiment of the invention, it is believed that it is not critical that the transalkylation reaction zone be any particular transalkylation zone. Rather, it is believed instead that the transalkylation zone may be any suitable transalkylation zone, such as those described in U.S. Pat. Nos. 4,008,290; 4,774,377; and 4,891,458. A beta zeolite catalyst, such as the beta-containing catalysts described in U.S. Pat. No. 6,835,862 B1, may be used in the transalkylation zone. The transalkylation reactor effluent stream exits bed 632 and transalkylation reactor 630 via line 638 and passes through heat exchanger 640, where the transalkylation reactor effluent stream may be cooled or heated, depending on the temperature of the transalkylation reactor effluent stream relative to the desired temperature in the alkylation reactor 650. After exiting heat exchanger 640, the transalkylation reactor effluent stream flows through line 642 and combines with ethylene from line 644 to produce the stream flowing through line 646. The alkylation reactor feed stream flowing in line 647 is formed by combining the stream flowing in line 646 with a recycled and cooled aliquot portion of the alkylation reactor effluent stream in line 662. Turbulence in lines 646 and 647 helps ensure that the ethylene concentration is uniform in the alkylation reactor feed stream as the stream enters alkylation reactor 650. The alkylation reactor 650 contains two beds of UZM-8 zeolite alkylation catalyst, 653 and 655, and the alkylation reactor feed stream enters bed 653. An effluent stream exits bed 653 and combines with an ethylene-containing stream flowing through line 648 to form the feed stream for bed 655. The introduction of ethylene between beds 653 and 655 is done in a manner so that the concentration of the ethylene in the feed stream to bed 655 is uniform. An effluent stream exits bed 655 and leaves alkylation reactor 650 via line 652. The alkylation reactor effluent stream in line 652 divides into two aliquot portions. One aliquot portion flows through line 654 to a downstream alkylation reactor or to a product separation zone, which is not shown. The other aliquot portion of the alkylation reactor effluent stream flows through line 658, enters heat exchanger 660 where the aliquot portion is cooled, flows through line 662, and then combines with the stream flowing through line 646.

Referring now to FIG. 7, ethylene enters via line 704 and combines with a benzene-containing stream flowing through line 702 to form the stream flowing through line 706. Turbulent flow in line 706 helps ensure good mixing and uniformity of the ethylene concentration in the feed stream as it enters alkylation reactor 710. The alkylation reactor 710 contains two beds of solid alkylation catalyst, 712 and 713, and the alkylation reactor feed stream enters bed 712. In bed 712, ethylene alkylates benzene to produce ethylbenzene, but it should be noted that, regarding this embodiment of the invention, it is believed that it is not critical that bed 712 be any particular alkylation catalyst bed. Rather, it is believed instead that the alkylation that occurs in bed 712 may be done in any suitable alkylation zone, even in an alkylation zone which is not in the same alkylation reactor as bed 713. Suitable alkylation zones for bed 12 include as those described in U.S. Pat. Nos. 4,008,290; 4,774,377; 4,891,458; and 6,835,862 B1. An effluent stream exits bed 712 and combines with a stream flowing through line 726 to form the feed stream for bed 713, which contains UZM-8 zeolite catalyst. The stream in line 726 is formed by combining an ethylene-containing stream in line 724 with a cooled aliquot portion of alkylation reactor effluent flowing through line 722. Turbulent flow in line 726 helps ensure good mixing and uniformity of the ethylene concentration in the stream in line 726 as it enters alkylation reactor 710. The introduction of the stream in line 726 between beds 712 and 713 is done in a manner so that the concentration of the ethylene in the feed stream to bed 713 is uniform. An effluent stream exits bed 713 and alkylation reactor 710 via line 714, and then divides into two aliquot portions. One aliquot portion passes through line 716 to another alkylation reactor or a product separation zone, which is not shown. The other aliquot portion of the reactor effluent stream flows through line 718, is cooled in heat exchanger 720, and then flows through line 722 to combine with the ethylene-containing stream in line 724, as described previously.

Referring now to FIG. 8, ethylene enters via line 824 and combines with a stream flowing through line 826 to form the stream flowing through line 828. The stream in line 826 is formed by combining benzene from line 876 and the stream flowing in line 866, which is an aliquot portion of the stream flowing in line 862 and which contains components from the bottoms stream of deethanizer column 860 and the overhead stream of benzene column 870. The stream flowing through line 828, which is the first alkylation reactor feed stream, contains ethylene, benzene, and recycled components, which may include recycled polyethylbenzenes, such as diethylbenzenes, triethylbenzenes, and heavier polyethylbenzenes. Turbulent flow helps ensure good mixing and uniformity of the ethylene concentration in the feed stream as it enters first alkylation reactor 830. The first alkylation reactor 830 contains two beds of solid alkylation catalyst, 832 and 834, and the first alkylation reactor feed stream enters bed 832. An effluent stream exits bed 832 and combines with an ethylene-containing stream flowing through line 836 to form the feed stream for bed 834. The introduction of ethylene between beds 832 and 834 is done in a manner so that the concentration of the ethylene in the feed stream for bed 834 is uniform. An effluent stream exits bed 834 and first alkylation reactor 830 via line 838, is cooled in heat exchanger 840, passes through line 842, and combines with ethylene from line 844 to produce the stream flowing through line 846. The second alkylation reactor feed stream flowing in line 847 is formed by combining the stream flowing in line 846 with the stream flowing in line 845, which is an aliquot portion of the recycle stream flowing through line 862. Turbulence in lines 846 and 847 helps ensure that the ethylene concentration is uniform in the second alkylation reactor feed stream as the stream enters second alkylation reactor 850. The second alkylation reactor 850 contains two beds of solid alkylation catalyst, 853 and 855, and the second alkylation reactor feed stream enters bed 853. An effluent stream exits bed 853 and combines with an ethylene-containing stream flowing through line 848 to form the feed stream for bed 855. The introduction of ethylene between beds 853 and 855 is done in a manner so that the concentration of the ethylene in the feed stream to bed 855 is uniform. An effluent stream exits bed 855 and leaves alkylation reactor 850 via line 852.

The effluent stream in line 852 enters deethanizer column 860, which separates lighter hydrocarbons, such as ethane and compounds lighter than ethane, from the entering stream in line 852. The separated components are recovered in an overhead stream in line 864 and routed to downstream processing, which is not shown. The bottom stream of deethanizer 860 flows through line 868 and divides into two aliquot portions. One aliquot portion flows through line 874 to heat exchanger 876. Heat exchanger 876 cools the aliquot portion to a temperature that is suitable for recycling to alkylation reactors 830 and 850 in the manner shown in FIG. 8. It should be pointed out that, in some variations of the embodiment shown in FIG. 8, heat exchanger 876 may not be required, due to the cooling effect that may accompany flashing of the stream in line 852 in conjunction with the deethanizing step. In any event, the stream in line 878 combines with the overhead stream in line 882 from benzene column 870, and the combined stream flows through line 862. The other aliquot portion of the deethanizer bottom stream in line 868 flows through line 872 to benzene column 870. The benzene column 870 separates the aliquot portion of the deethanizer bottom stream by distillation into two streams. The benzene column overhead stream comprising benzene exits the benzene column 870 through line 882 and combines with the stream flowing in line 878 for recycling, as described previously. A benzene column bottom stream comprising the product ethylbenzene and the byproducts including polyethylbenzenes exits the benzene column in line 884 and enters ethylbenzene column 880. Ethylbenzene column 880 separates the benzene column bottom stream by distillation into two streams. An ethylbenzene column overhead stream comprising the product ethylbenzene exits the ethylbenzene column 880 in line 886 and is recovered from the process. An ethylbenzene column bottom stream comprising byproduct ethylbenzenes and diphenylethanes exits the ethylbenzene column 880 in line 888 and is sent to further processing facilities, such as to a polyethylbenzene column, which is not shown in FIG. 8.

EXAMPLES

The following abbreviations will be used in the examples:
Al (Osec-Bu)$_3$—aluminum tri-sec-butoxide
DEDMAOH—diethyldimethylammonium hydroxide
ETMAOH—ethyltrimethylammonium hydroxide
TMABr—tetramethylammonium bromide
In the examples that follow, ethylene conversion is defined as the difference between the ethylene expressed in wt-% of the stream entering the reactor and the ethylene expressed in wt-% of the stream exiting the reactor divided by the ethylene expressed in wt-% of the stream entering the reactor. The selectivity of a component is defined as the difference between the number of carbon atoms in molecules of the component exiting the reactor and the number of carbon atoms in molecules of the component entering the reactor, divided by the total number of carbon atoms in molecules of ethylene converted and molecules of benzene converted, and multiplied by 100. The total of the selectivities of ethylbenzene (EB), diethylbenzene (DEB), triethylbenzene (TEB), and tetraethylbenzene (TeEB) accounts for the total selectivity to EB that would be produced if all the diethylbenzene, triethylbenzene, and tetraethylbenzene in the net reactor effluent were transalkylated to EB in a typical transalkylation zone and subsequently recovered. The total of the selectivities of butylbenzene ($C_4$-Bz), butyl-ethylbenzene ($C_4$-EB), and butyl-diethylbenzene ($C_4$-DEB) and the total of the selectivities of diphenylethane (DPE) and ethyidiphenylethane (EDPE) account for undesirable byproducts that cannot be readily transalkylated to EB in a typical transalkylation zone and therefore typically represent a loss of EB production.

Example 1

A fresh alkylation catalyst comprising 70 wt-% zeolite beta and 30 wt-% alumina binder was prepared and is designated as Catalyst A. The zeolite beta for Catalyst A was prepared in substantially the same manner as described in U.S. Pat. No. 5,522,984.

An aluminosilicate reaction mixture was prepared in the following manner. A 7329.73 g portion of DEDMAOH (20% aq) was added to a tank. A 804.38 g portion of Al (Osec-Bu)$_3$ (95%+) was added to the tank, and the resulting solution was thoroughly mixed for 45 min. A 2000 g quantity of deionized water was then added to the solution, followed by the addition of a 2526.96 g portion of precipitated silica (Ultrasil™ VN SP3, 89% SiO$_2$). Next, a solution of 126.69 g of NaOH dissolved in 212.25 g of deionized water was prepared and added to the reaction mixture and the reaction mixture was thoroughly mixed for 30 min. The reaction mixture was then transferred to a 19-L stirred reactor. The tank was rinsed with 1000 g of deionized water and the rinse was transferred to the reactor and mixed into the reaction mixture. The reaction mixture was heated in 3 hr to 150° C. and digested at 150° C. for 290 hr. A solid product was collected by filtering, washed with deionized water, and dried at 50° C. The isolated product was identified as UZM-8 by powder x-ray diffraction analysis. Elemental analysis revealed the composition of the isolated product to consist of the elemental mole ratios of Si/Al=11.77, Na/Al=0.26, N/Al=2.03, and C/N=3.04. The isolated product was ammonium ion-exchanged using an ion exchange solution of 1 part by weight of NH$_4$NO$_3$, 10 parts by weight of deionized water, and 1 part by weight of the isolated product at about 75° C. for 3 hr, and the solids were collected by filtering. The ammonium ion exchange and filtration was repeated two more times, and the triple ammonium ion-exchanged material was washed with deionized water and dried at about 50° C. A sample of the dried material was calcined by heating to 540° C. and holding at that temperature for 2 hr in the presence of flowing nitrogen, and then switching to flowing air and holding at that temperature for 14 hr. Thereafter the BET surface area was found to be 481 m$^2$/g and the micropore volume was 0.14 cc/g. Another sample of the dried material was then formulated into a catalyst comprising 80 wt-% UZM-8 and 20 wt-% alumina. The extrusion was done using HNO$_3$-peptized Al$_2$O$_3$ as a binder and 3.0 wt-% based on the weight of the UZM-8 and the alumina of Solka-Floc™ powdered cellulose (BW-40; International Fiber Corp., North Tonawanda, N.Y., USA) as an extrusion aid to obtain 1.6 mm (⅟₁₆ in) diameter extrudates. The extrudates were activated in a muffle oven by heating to 538° C. and holding at that temperature for 1 hr in the presence of flowing nitrogen, and then switching to flowing air and holding at that temperature for 15 hr. This catalyst is designated as Catalyst B.

An aluminosilicate reaction mixture was prepared in the following manner. In a beaker, a 32.77 g portion of Al (Osec-Bu)$_3$ (95%+) was dissolved in 538.39 g of DEDMAOH (20% aq) and thoroughly mixed for 10 min. A 500 g quantity of deionized water was added to the beaker. A 175 g portion of precipitated silica (Ultrasil™ VN SP3, 89% SiO$_2$) was slowly added, and the reaction mixture was thoroughly mixed for 10 min. In a separate beaker, a 6.58 g portion of NaBr and a 23.86 g portion of TMABr were dissolved in 123 g of deionized water, the resulting solution was added to the reaction mixture and then the reaction mixture was thoroughly mixed for 10 min. Next, a 14 g (on a volatile free basis) portion of finely ground UZM-8 seed was added to the reaction mixture, and the reaction mixture was thoroughly mixed for 20 min. The reaction mixture was then transferred to a 2-L stirred reactor and heated to 150° C. in 2 hr and digested at 150° C. for 166 hr. A solid product was collected by centrifugation, washed with deionized water, and dried in air. The isolated product was identified as UZM-8 by powder x-ray diffraction analysis. Elemental analysis revealed the composition of the isolated product to consist of the elemental mole ratios of Si/Al=15.69 and Na/Al=0.74. The isolated product was ammonium ion-exchanged, washed, and dried in the manner described for Catalyst B. One sample of the dried material was calcined in the manner described for Catalyst B, and thereafter for this sample the BET surface area was found to be 413 m$^2$/g and the micropore volume was 0.146 cc/g. Another sample of the dried material was formulated into a catalyst comprising 80 wt-% UZM-8 and 20 wt-% alumina and activated in the manner described for Catalyst B, except that 0.5 wt-% based on the weight of the UZM-8 and the binder of Methocel™ methylcellulose (A4M; Dow Chemical Co., Midland, Mich, USA) was used as the extrusion aid. This catalyst is designated as Catalyst C.

An aluminosilicate reaction mixture was prepared in the following manner. In a baffled tank, a 6 g (on a volatile free basis) portion of dry UZM-8 seed was added to 706.2 g of deionized water and thoroughly mixed. In a separate beaker, a 38.3 g portion of liquid sodium aluminate, a 108.5 g portion of ETMAOH (20% aq), and a 4 g portion of a 50% NaOH solution were mixed, and then added to the tank. Next, 137.2 grams of precipitated silica (Ultrasil™ VN SP3, 89% SiO$_2$) was added in 5 minutes to the tank, and the reaction mixture was thoroughly mixed for 20 minutes. The reaction mixture was then transferred to a 2-L stirred reactor. The reaction mixture was then heated in 2 hr to 150° C. and digested at 150° C. for 165 hr. A solid product was collected by centrifugation, washed with deionized water, and dried at 50° C. The isolated product was identified as UZM-8 by powder x-ray diffraction analysis. Elemental analysis revealed the composition of the isolated product to consist of the elemental mole ratios of Si/Al=10.22, Na/Al=0.49, N/Al=0.74, and C/N=5.21. The isolated product was ammonium ion-exchanged, washed, and dried in the manner described for Catalyst B. One sample of the dried material was calcined in the manner described for Catalyst B, and thereafter for this sample the BET surface area was found to be 505 m$^2$/g and the micropore volume was 0.134 cc/g. Another sample of the dried material was then formulated into a catalyst and activated in the manner described for Catalyst B, except the catalyst comprised 70 wt-% UZM-8 and 30 wt-% alumina. This catalyst is designated as Catalyst D.

An aluminosilicate reaction mixture was prepared in the following manner. In a beaker, a 84.88 g portion of Al (Osec-Bu)$_3$ (95%+) was added to a 386.73 g portion of DEDMAOH (20% aq) with vigorous mixing. A 266.66 g portion of precipitated silica (Ultrasil™ VN SP3, 89% SiO$_2$) was added to the reaction mixture. A quantity of 600 g of deionized water was added to the reaction mixture. Then a solution containing 13.37 g of NaOH dissolved in 48 g of deionized water was added to the reaction mixture with mixing. The reaction mixture was thoroughly mixed for 20 minutes. A 140 g portion of slurry UZM-8 seed was added to the reaction mixture and was thoroughly mixed for 20 minutes. A slurry UZM-8 seed is a reaction mixture used to make UZM-8 zeolite after digestion and prior to isolation by filtering, centrifugation, or other means. The reaction mixture was then transferred to a 2-L stirred reactor, heated to 150° C. in 2 hr, and then digested at 150° C. for 216 hr. A solid product was collected by filtering, washed with deionized water, and dried at 50° C. The isolated product was identified as UZM-8 by powder x-ray diffraction analysis.

Elemental analysis revealed the composition of the isolated product to consist of the elemental mole ratios of Si/Al=11.00, Na/Al=0.47, N/Al=1.17, and C/N=5.53. The isolated product was ammonium ion-exchanged, washed, and dried in the manner described for Catalyst B. One sample of the dried material was calcined in the manner described for Catalyst B, and thereafter for this sample the BET surface area was found to be 493 m$^2$/g and the micropore volume was 0.13 cc/g. Another sample of the dried material was formulated into a catalyst and activated in the manner described for Catalyst D. This catalyst is designated as Catalyst E.

An aluminosilicate reaction mixture was prepared in the following manner. In a tank, a 2115.55 g portion of DEDMAOH (20% aq) was added to 10 kg deionized water. A 781.88 g portion of liquid sodium aluminate was added slowly to the reaction mixture, and the reaction mixture was thoroughly mixed for 20 min. A 2877.01 g portion of precipitated silica (Ultrasil™ VN SP3, 89% SiO$_2$) was slowly added to the reaction mixture and thoroughly mixed for 20 min. A 1400 g portion of slurry UZM-8 seed was added to the reaction mixture and the reaction mixture was mixed thoroughly for an additional 20 minutes. The reaction mixture was then transferred to a 19-L stirred reactor. The tank was rinsed with 525 g of deionized water and the rinse was transferred to the reactor and mixed into the reaction mixture. The reaction mixture was heated to 150° C. in 6 hours and digested at 150° C. for 138 hours. A solid product was collected by centrifugation, washed with deionized water, and dried at 50° C. The isolated product was identified as UZM-8 by powder x-ray diffraction analysis. Elemental analysis revealed the composition of the isolated product to consist of the elemental mole ratios of Si/Al=10.46, Na/Al=0.49, N/Al=0.59, and C/N=6.22. The isolated product was ammonium ion-exchanged, washed, and dried in the manner described for Catalyst B. One sample of the dried material was calcined in the manner described for Catalyst B, and thereafter for this sample the BET surface area was found to be 530 m$^2$/g and the micropore volume was 0.135 cc/g. Another sample of the dried material was formulated into a catalyst and activated in the manner described for Catalyst D. This catalyst is designated as Catalyst F.

Example 2

The experimental procedure used in the tests for Example 1 was as follows. A volume of the catalyst to be tested was loaded into a cylindrical reactor. The reactor was equipped with a thermocouple in a thermowell located to measure temperatures at distances along the length of the fixed catalyst bed. Dry benzene was passed through the reactor at 260° C. (500° F.) and at a benzene LHSV of 6.7 hr$^{-1}$ for 24 hours.

Subsequently, the flow of fresh benzene was adjusted and the reactor inlet temperature was lowered to a temperature about 50° C. (90° F.) below the desired distance average bed temperature (DABT) for the initial testing conditions. As used herein, DABT means the temperature calculated by plotting the catalyst bed temperature versus distance along the catalyst bed, computing the area under the curve from the inlet to the outlet of the catalyst bed, and dividing the area by the length of the catalyst bed. Fresh ethylene was introduced into the reactor. Then a portion of the reactor effluent was recycled so that a combined feed of the fresh benzene, the fresh ethylene, and the recycled reactor effluent flowed to the reactor. The reactor inlet temperature was adjusted to maintain the desired DABT while the reactor effluent was sampled and analyzed. Then the reactor inlet temperature and/or the amount of recycled reactor effluent was adjusted, and the reactor effluent was sampled again. This process was repeated until measurements and samples were obtained at all of the desired DABTs and effluent recycle ratios (R/FF). It is believed that minimal catalyst deactivation occurred over the duration that the performance of each catalyst was measured.

The ethylene WHSV was about 0.76 hr$^{-1}$ for the tests of Catalyst A and about 0.90 to 0.92 hr$^{-1}$ for the tests of Catalysts B and C. The molar ratio of fresh benzene to fresh ethylene for these tests was about 2. The R/FF for these tests was about 4 or about 8. Because the molar ratio of aryl groups per ethyl group is essentially the same in the combined reactor feed stream and the total reactor effluent stream, the molar ratio of aryl groups per ethyl group is not significantly affected by recycling any portion of the reactor effluent stream.

Figure 9:
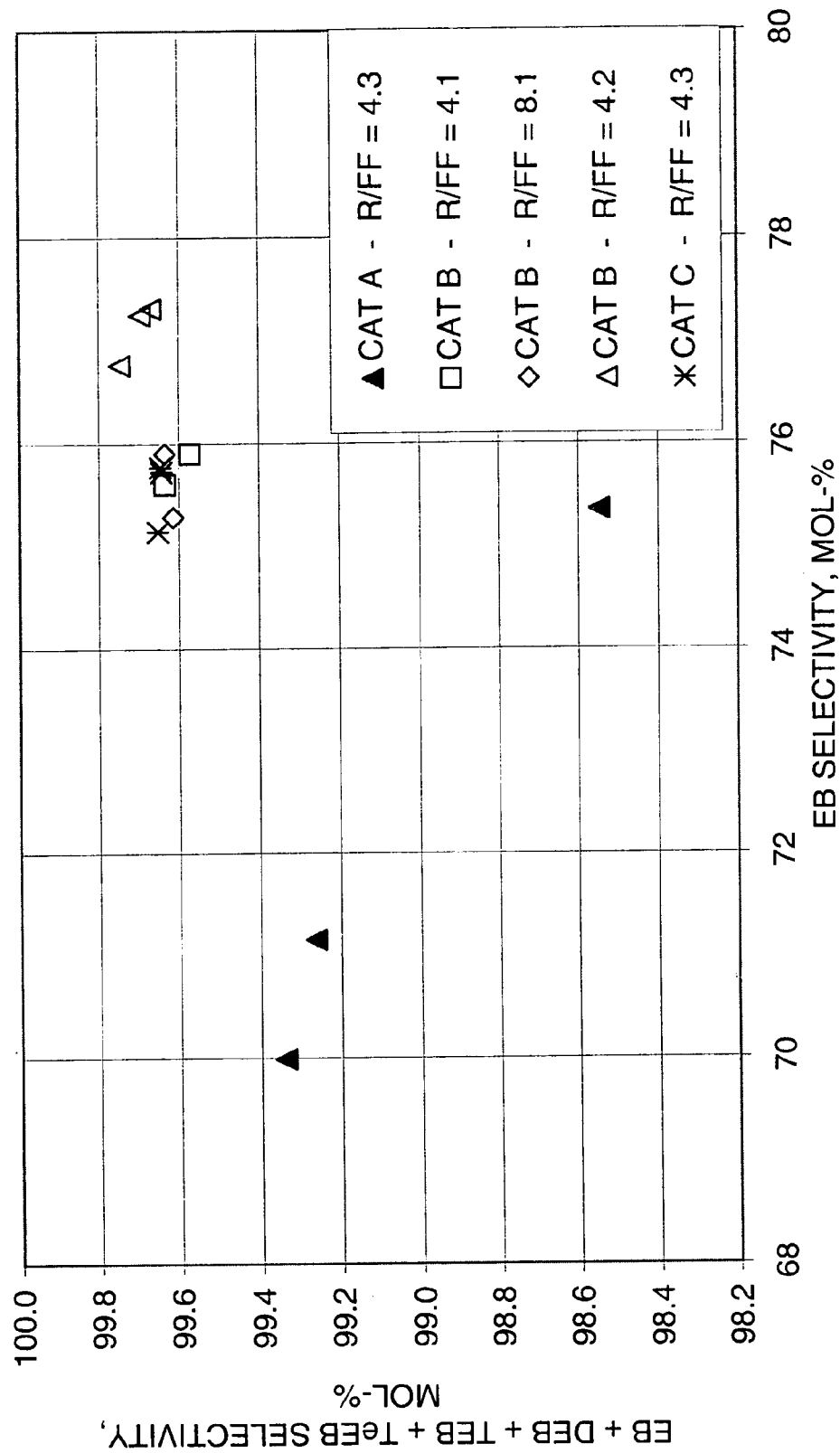
FIGS. 9-12 are graphs showing the results of tests using reactor effluent recycle.
Figure 10:
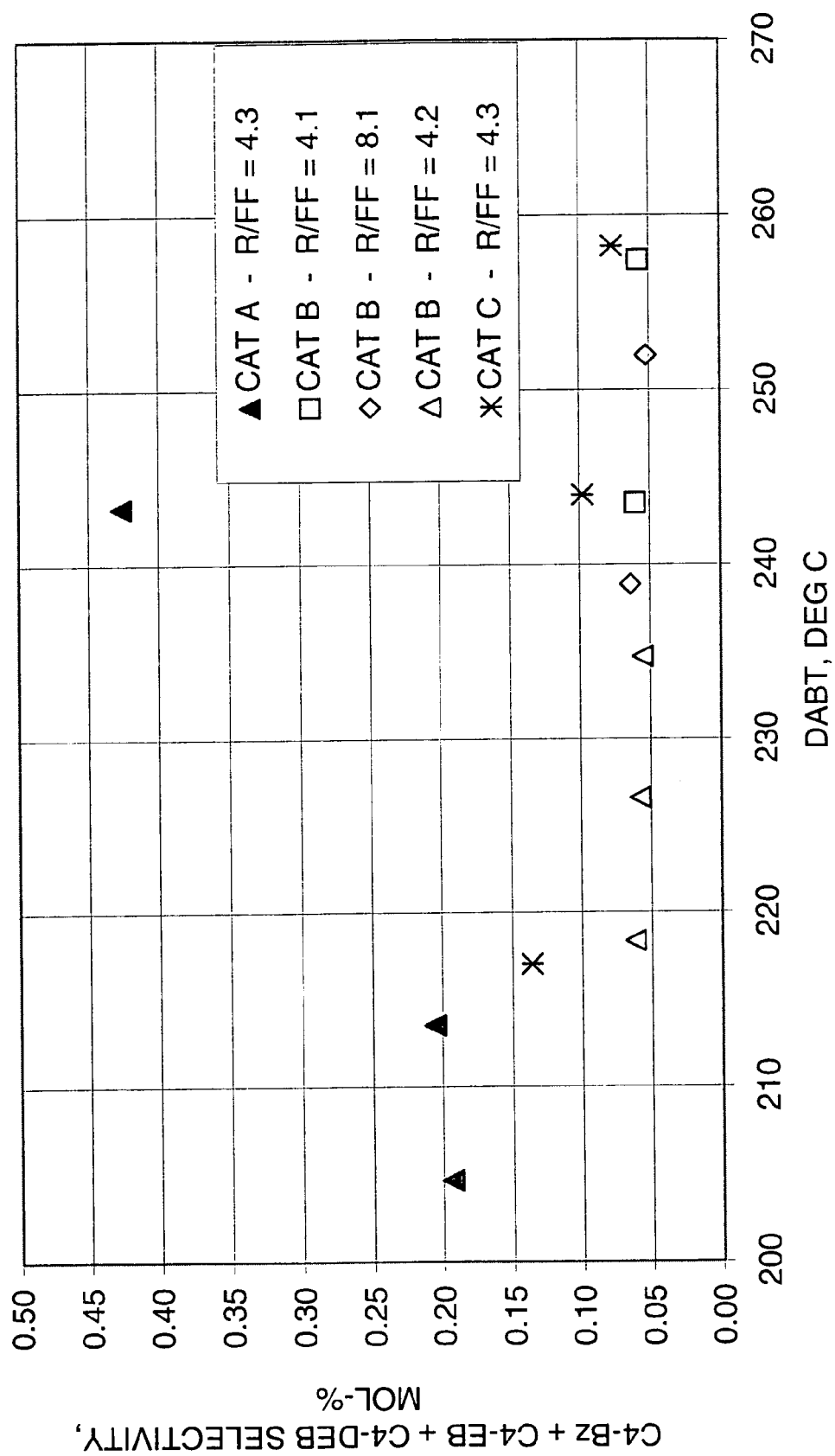
Figure 11:
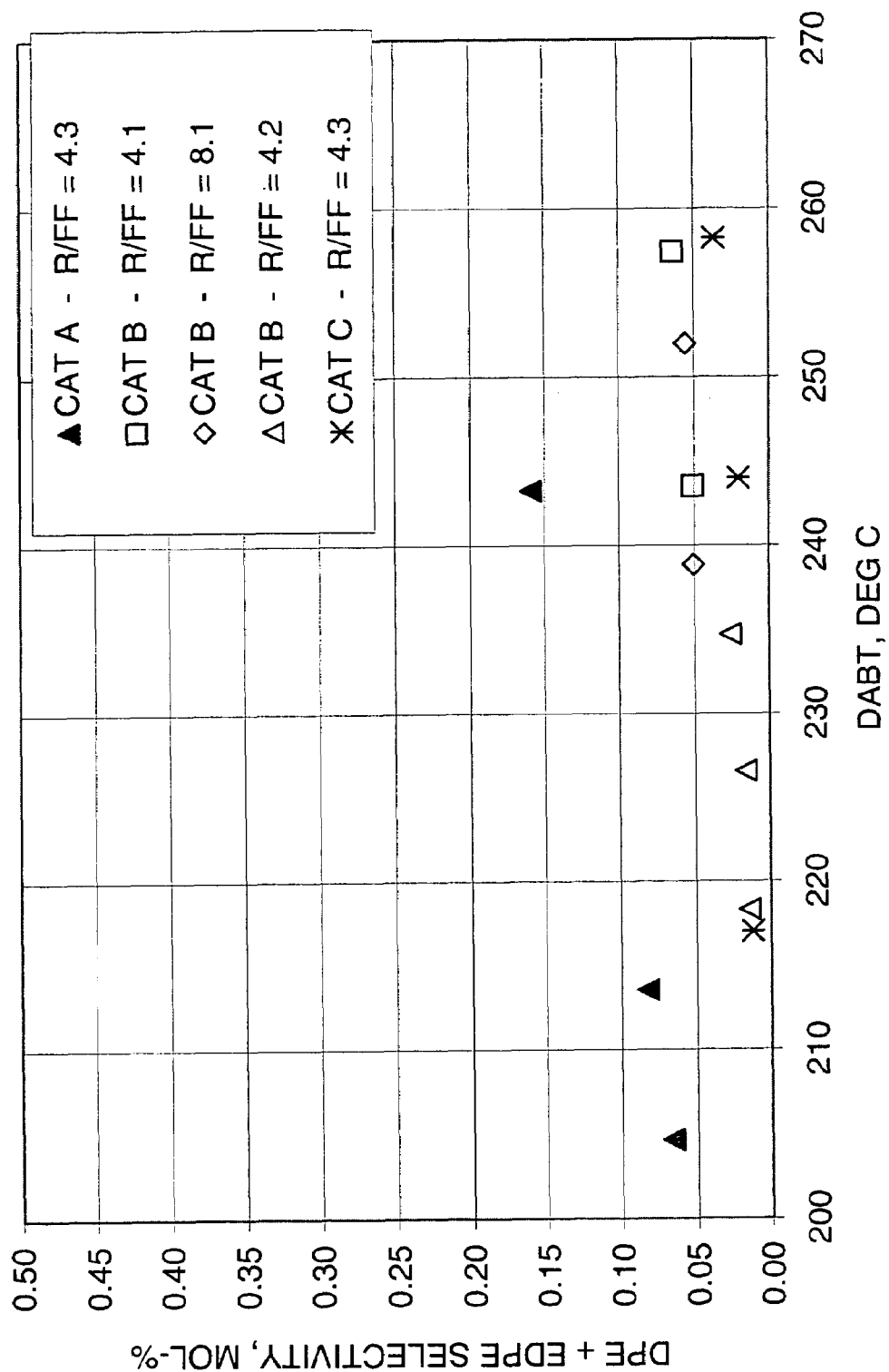

Results are shown in FIGS. 9-11. Additional results of tests done at DABTs from 214 to 218° C. (416 to 425° F.) and from 239 to 244° C. (462 to 471° F.) are shown in Table 1. Each result in FIGS. 9-11 and in Table 1 is an average from measurements and/or analyses at each test condition. FIG. 9 is a graph of total selectivity to (EB+DEB+TEB+TeEB) versus selectivity to EB and shows that, in comparison with a process using Catalyst A, a process using Catalyst B or C has a higher total selectivity to (EB+DEB+TEB+TeEB) at a given EB selectivity. FIG. 10 is a graph of total selectivity to (C$_4$-Bz+C$_4$-EB+C$_4$-DEB) versus DABT and shows that a process using Catalyst B or C has a lower total selectivity to (C$_4$-Bz+C$_4$-EB+C$_4$-DEB) at a given DABT than a process using Catalyst A. FIG. 11 is a graph of total selectivity to (DPE+EDPE) versus DABT and shows that a process using Catalyst B or C has a lower total selectivity to (DPE+EDPE) at a given DABT than a process using Catalyst A. These results indicate that an alkylation-transalkylation combination process using Catalysts B or C for alkylation would produce more EB than a process using Catalyst A.

Tests 3 and 5 for Catalyst B in Table 1 show that despite nearly doubling the R/FF from 4.1 to 8.1 the selectivity to EB and each of the total selectivities to (EB+DEB+TEB+TeEB), ($C_4$-Bz+$C_4$-EB+$C_4$-DEB ), and (DPE+EDPE) remained nearly the same.

At about the same DABT and R/FF, a change in Si/$Al_2$ molar ratio of the UZM-8 zeolite from 31.38 (Catalyst C) to 23.54 (Catalyst B) provided essentially the same or higher selectivity to EB and total selectivity to (EB+DEB+TEB+TeEB). At 4.1-4.3 R/FF, tests 4 and 7 show this at 217-218° C. (423-425° F.) DABT while tests 3 and 6 show this at 244° C. (470-471° F.) DABT. In addition, the total selectivity to ($C_4$-Bz+$C_4$-EB+$C_4$-DEB ) decreased.

Example 3

The experimental procedure used in the tests for Example 3 was the same as for Example 2, except that for the tests for Example 3 the catalyst was Catalyst D, the ethylene WHSV was about 0.89 $hr^{-1}$, and the molar ratio of fresh benzene to fresh ethylene was about 1.8. In Example 3, the R/FF was about 4.3 during tests 1 and 2. Subsequently, the reactor effluent recycle was stopped during test 3. It is believed that minimal catalyst deactivation occurred over the duration that the tests were performed.

The results shown in Table 2 are averages from measurements and/or analyses at each test condition. Table 2 shows that at nearly the same ethylene conversion recycling reactor effluent increased the EB selectivity and the total selectivity to (EB+DEB+TEB+TeEB), and decreased the total selectivities to ($C_4$-Bz+$C_4$-EB+$C_4$-DEB ) and (DPE+EDPE). In addition, recycling reactor effluent decreased by at least 66% the selectivities to non-aromatics and to compounds heavier than DPE and EDPE.

Example 4

A volume of the catalyst to be tested was loaded into the cylindrical reactor described in Example 1. Dry benzene was passed through the reactor at 260° C. (500° F.) and at a benzene LHSV of 6.7 $hr^{-1}$ for 24 hours. Subsequently, the flow of fresh benzene was adjusted and the reactor inlet temperature was lowered to a temperature about 50° C. (90° F.) below the desired DABT for the initial testing conditions. Fresh ethylene was introduced into the reactor. The molar ratio of fresh benzene to fresh ethylene for these tests was about 2. Then a portion of the reactor effluent was recycled so that a combined feed of the fresh benzene, the fresh ethylene, and the recycled reactor effluent flowed to the reactor. The reactor inlet temperature was adjusted to maintain the desired DABT. The temperature within the catalyst bed rose as the incoming feed contacted the catalyst due to the exothermic nature of the reaction. At times during a period (e.g., 100 hours) at test conditions, temperature profiles (bed temperature versus distance through the bed) were plotted. The rate of catalyst deactivation was taken to be the rate of progression of these temperature profiles through the bed. The position of each temperature profile was defined by the end of the active zone, which was a measure of the end of the temperature rise in the temperature profile. On a temperature profile, the end of the active zone was the distance in the bed at the intersection of the linear extrapolation of the linear part of the temperature rise and a horizontal line at the maximum bed temperature. After the rate of deactivation was determined at one set of test conditions, the rates of fresh ethylene and fresh benzene were increased (higher LHSV) in order to accelerate the rate of deactivation.

The results are shown in Table 3. At the low WHSV conditions and at comparable times on stream, the deactivation rate of Catalyst E was one-tenth that of Catalyst A. After the ethylene WHSV was increased, the deactivation rate of Catalyst A decreased only slightly and the end of the active zone continued to move toward the outlet of the catalyst bed as Catalyst A continued to deactivate. During comparable times on stream, the deactivation rate of Catalyst E also decreased and remained much less than that of Catalyst A. Indeed, at the higher WHSV conditions the deactivation rate of Catalyst E decreased by so much that the end of the active zone stopped moving toward the outlet of the catalyst bed and instead moved toward the inlet of the catalyst bed. This is evidenced by the negative slope (i.e., −0.0004) of the plot of the position of the end of the active catalyst zone versus time on stream. This in turn indicates that the using Catalyst E with reactor effluent recycle in an alkylation process would permit increased ethylene throughput and therefore increased alkylate production for longer periods of time than would use of Catalyst A.

Example 5

The experimental procedure used in the tests for Example 5 was the same as for Example 2, except that Catalyst F was used, the olefin was propylene, propylene WHSV was about 1.07 $hr^{-1}$, and the molar ratio of fresh benzene to fresh propylene was about 2.9. The R/FF was 4.9, 7.2, and 11.4, and the propylene concentration in the combined feed was 2.7 wt-%, 1.9 wt-%, and 1.3 wt-%, respectively. The molar ratio of aryl groups per propyl group is essentially the same in the combined reactor feed stream and the total reactor effluent stream, and therefore the molar ratio of aryl groups per propyl group is not significantly affected by recycling any portion of the reactor effluent stream. It is believed that minimal catalyst deactivation occurred over the duration that the tests were performed.

Figure 12:
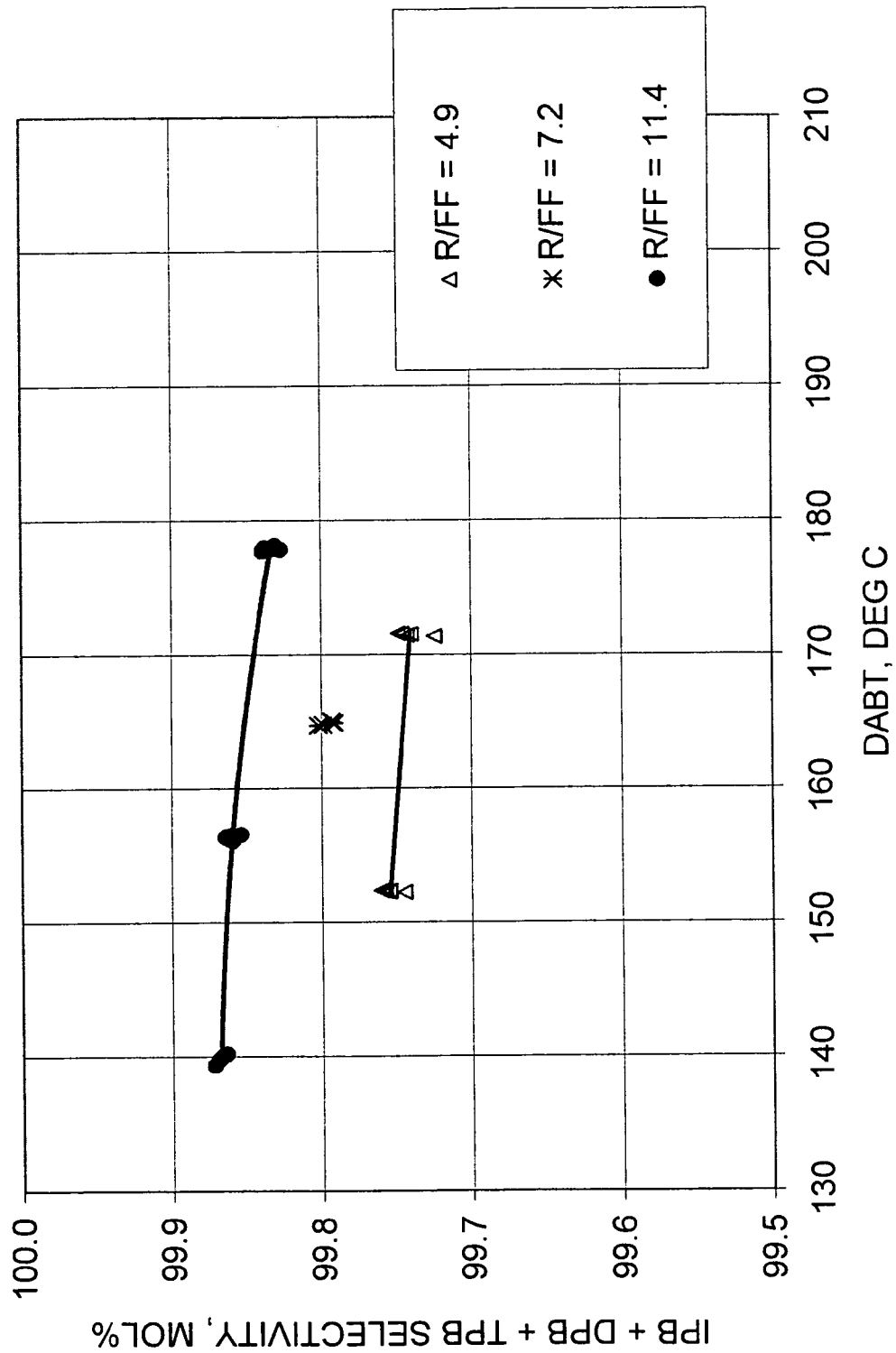

The results shown in FIG. 12 are averages from measurements and/or analyses at each test condition. FIG. 12 shows that recycling more reactor effluent increased the total selectivity to cumene (IPB), dipropylbenzene (DPB), and tripropylbenzene (TPB).

Example 6

The experimental procedure used in the tests for Example 6 was the same as for Example 4, except that Catalyst E was used, the olefin was propylene, and the molar ratio of fresh benzene to fresh propylene was about 2.4.

The results are shown in Table 4. At the low WHSV conditions and at comparable times on stream, the deactivation rate of Catalyst E was about 38% of that of Catalyst A. After the ethylene WHSV was increased, the deactivation rate of Catalyst A increased by a factor of 5 while during comparable times on stream the deactivation rate of Catalyst E decreased.

TABLE 1

| | Catalyst | | | | | | |
|---|---|---|---|---|---|---|---|
| | A | | B | | C | | |
| Test | 1 | 2 | 3 | 4 | 5 | 6 | 7 |
| Recycle/fresh feed ratio, wt/wt | 4.3 | 4.3 | 4.1 | 4.1 | 8.1 | 4.3 | 4.3 |
| Olefin concentration in combined feed, wt-% | 2.9 | 2.9 | 3.0 | 3.0 | 1.7 | 2.9 | 2.9 |
| Inlet temperature, °C. (°F.) | 193 (379) | 168 (335) | 194 (382) | 172 (342) | 198 (389) | 195 (383) | 170 (338) |
| DABT, °C. (°F.) | 243 (470) | 214 (416) | 244 (470) | 218 (425) | 239 (462) | 244 (471) | 217 (423) |
| Ethylene WHSV, hr$^{-1}$ | 0.76 | 0.76 | 0.90 | 0.90 | 0.90 | 0.92 | 0.92 |
| Ethylene conversion, mol-% | 99.83 | 99.92 | 99.92 | 99.88 | 99.88 | 99.91 | 99.63 |
| Selectivity, mol-% | | | | | | | |
| EB | 75.70 | 71.15 | 75.61 | 76.76 | 75.90 | 75.11 | 75.77 |
| EB + DEB + TEB + TeEB | 98.55 | 99.26 | 99.64 | 99.75 | 99.64 | 99.65 | 99.65 |
| $C_4$-Bz + $C_4$-EB + $C_4$-DEB | 0.43 | 0.21 | 0.06 | 0.06 | 0.06 | 0.10 | 0.14 |
| DPE + EDPE | 0.16 | 0.08 | 0.05 | 0.01 | 0.05 | 0.02 | 0.01 |

TABLE 2

| | Catalyst D | | |
|---|---|---|---|
| Test | 1 | 2 | 3 |
| Recycle/fresh feed ratio, wt/wt | 4.3 | 4.3 | 0 |
| Olefin concentration in combined feed, wt-% | 3.2 | 3.2 | 17.1 |
| Inlet temperature, °C. (°F.) | 208 (406) | 163 (325) | 226 (439) |
| Temperature rise, °C. (°F.) | 45 (81) | 44 (79) | 37 (67) |
| Ethylene conversion, mol-% | 99.7 | 99.7 | 99.9 |
| Selectivity, mol-% | | | |
| EB | 73.1 | 73.1 | 60.9 |
| EB + DEB + TEB + TeEB | 99.55 | 99.61 | 97.76 |
| $C_4$-Bz + $C_4$-EB + $C_4$-DEB | 0.06 | 0.13 | 0.65 |
| DPE + EDPE | 0.05 | 0.02 | 0.08 |

TABLE 3

| | Catalyst | |
|---|---|---|
| | A | E |
| Low WHSV Conditions | | |
| Recycle/fresh feed ratio, wt/wt | 4.3 | 4.2 |
| Olefin concentration in combined feed, wt-% | 2.9 | 2.9 |
| Inlet temperature, °C. (°F.) | 168 (334) | 168 (334) |
| DABT, °C. (°F.) | 215 (419) | 215 (419) |
| Ethylene WHSV, hr$^{-1}$ | 0.77 | 0.84 |
| Deactivation rate, distance/unit time | 0.003 | 0.0003 |
| High WHSV Conditions | | |
| Recycle/fresh feed ratio, wt/wt | 2.9 | 2.8 |
| Olefin concentration in combined feed, wt-% | 4.0 | 4.0 |
| Inlet temperature, °C. (°F.) | 172 (342) | 174 (345) |
| Ethylene WHSV, hr$^{-1}$ | 1.12 | 1.26 |
| Deactivation rate, distance/unit time | 0.002 | −0.0004 |

TABLE 4

| | Catalyst | |
|---|---|---|
| | A | E |
| Low WHSV Conditions | | |
| Recycle/fresh feed ratio, wt/wt | 4.8 | 4.9 |
| Olefin concentration in combined feed, wt-% | 3.2 | 3.1 |
| Inlet temperature, °C. (°F.) | 140 (284) | 141 (286) |

TABLE 4-continued

| | Catalyst | |
|---|---|---|
| | A | E |
| DABT, °C. (°F.) | 161 (322) | 161 (322) |
| Ethylene WHSV, hr$^{-1}$ | 0.91 | 1.07 |
| Deactivation rate, distance/unit time | 0.0016 | 0.0006 |
| High WHSV Conditions | | |
| Recycle/fresh feed ratio, wt/wt | 3.0 | 3.0 |
| Olefin concentration in combined feed, wt-% | 4.7 | 4.7 |
| Inlet temperature, °C. (°F.) | 141 (286) | 142 (288) |
| Ethylene WHSV, hr$^{-1}$ | 1.88 | 2.03 |
| Deactivation rate, distance/unit time | 0.0085 | 0.0005 |

What is claimed is:

1. An alkylation process for producing a monoalkylated aromatic, the process comprising:

a) passing an aromatic feedstock comprising a feed aromatic, an olefinic feedstock comprising a $C_2$-$C_4$ olefin, and an additional stream comprising an alkylated derivative of the feed aromatic having from one to six more $C_2$-$C_4$ alkyl groups than the feed aromatic, to an alkylation catalyst bed containing a solid catalyst, wherein the solid catalyst comprises a microporous crystalline zeolite having a layered framework of at least $AlO_2$ and $SiO_2$ tetrahedral units and a composition on an as-synthesized and anhydrous basis expressed by an empirical formula of:

$$M_m^{n+}R_r^{p+}Al_{1-x}E_xSi_yO_z$$

where M is at least one exchangeable cation, "m" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation:

$$z=(m \cdot n + r \cdot p + 3 + 4 \cdot y)/2$$

and is characterized in that it has the x-ray diffraction pattern having at least the d spacings and intensities set forth in Table A:

TABLE A

| 2-θ | d(Å) | I/I₀ % |
|---|---|---|
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs | b) alkylating the feed aromatic with the $C_2$-$C_4$ olefin in the alkylation catalyst bed in the presence of the solid catalyst at alkylation conditions to form a monoalkylated aromatic, wherein the monoalkylated aromatic has one more $C_2$-$C_4$ alkyl group than the feed aromatic; and c) withdrawing an effluent stream comprising the monoalkylated aromatic from the alkylation catalyst bed.

2. The process of claim 1 wherein the alkylation conditions comprise a concentration of the $C_2$-$C_4$ olefin based on the weight of the feed aromatic, the $C_2$-$C_4$ olefin, and the alkylated derivative of the feed aromatic passed to the alkylation catalyst bed in Step (a) of at most 17 wt-%.

3. The process of claim 2 wherein the concentration is at most 10.0 wt-%.

4. The process of claim 2 wherein the concentration is at most 5.0 wt-%.

5. The process of claim 2 wherein the concentration is at least 0.1 wt-%.

6. The process of claim 2 wherein the concentration is at least 1.5 wt-%.

7. The process of claim 1 wherein the alkylated derivative of the feed aromatic has two more $C_2$-$C_4$ alkyl groups than the feed aromatic.

8. The process of claim 1 further characterized in that the additional stream comprises an aliquot portion of the effluent stream.

9. The process of claim 8 further characterized in that the alkylation conditions comprise a weight ratio of the aliquot portion of the effluent stream to the feed aromatic and the $C_2$-$C_4$ olefin passed to the alkylation catalyst bed in Step (a) of at least 0.1.

10. The process of claim 9 wherein the weight ratio is at least 1.0.

11. The process of claim 9 wherein the weight ratio is at least 2.5.

12. The process of claim 9 wherein the weight ratio is at least 4.0.

13. The process of claim 1 further characterized in that the effluent stream comprises the alkylated derivative of the feed aromatic, at least a portion of the effluent stream is separated into a recycle stream comprising the alkylated derivative of the feed aromatic and a product stream comprising the monoalkylated aromatic, and the additional stream is formed from at least a portion of the recycle stream.

14. The process of claim 1 further characterized in that the alkylation conditions comprise a molar ratio of aryl groups to the $C_2$-$C_4$ alkyl group of at most 6.

15. The process of claim 14 further characterized in that the molar ratio of aryl groups to the $C_2$-$C_4$ alkyl group is at most 3.

16. The process of claim 1 wherein the feed aromatic is selected from the group consisting of benzene, naphthalene, anthracene, tetralin, phenanthrene, and alkylated derivatives thereof.

17. The process of claim 1 wherein the feed aromatic comprises benzene, the feed olefin comprises ethylene, and the monoalkylated aromatic comprises ethylbenzene.

18. The process of claim 1 wherein the feed aromatic comprises benzene, the feed olefin comprises propylene, and the monoalkylated aromatic comprises cumene.

19. The process of claim 1 wherein the microporous crystalline zeolite is ion-exchanged and contains less than 0.1 wt-% of alkali and alkaline earth metals.

20. The process of claim 1 wherein the microporous crystalline zeolite is ion-exchanged and contains less than 0.02 wt-% of alkali and alkaline earth metals.

21. The process of claim 1 wherein the microporous crystalline zeolite is calcined and is characterized in that it has the x-ray diffraction pattern having at least the d spacings and intensities set forth in Table B:

TABLE B

| 2-θ | d(Å) | I/I₀ % |
|---|---|---|
| 4.05-4.60 | 21.80-19.19 | w-m |
| 7.00-7.55 | 12.62-11.70 | m-vs |
| 8.55-9.15 | 10.33-9.66 | w-vs |
| 12.55-13.15 | 7.05-6.73 | w |
| 14.30-14.90 | 6.19-5.94 | m-vs |
| 19.55-20.35 | 4.54-4.36 | w-m |
| 22.35-23.10 | 3.97-3.85 | m-vs |
| 24.95-25.85 | 3.57-3.44 | w-m |
| 25.95-26.75 | 3.43-3.33 | m-s |

22. The process of claim 1 wherein the microporous crystalline zeolite is UZM-8.

23. The process of claim 1 wherein the solid catalyst contains a binder.

24. An alkylation process for producing ethylbenzene, the process comprising:

a) passing an aromatic feedstock comprising benzene, an olefinic feedstock comprising ethylene, and an aliquot portion of an effluent stream comprising diethylbenzene to an alkylation catalyst bed containing a solid catalyst, wherein the solid catalyst comprises a microporous crystalline zeolite having a layered framework of at least $AlO_2$ and $SiO_2$ tetrahedral units and a composition on an as-synthesized and anhydrous basis expressed by an empirical formula of:

$$M_m^{n+}R_r^{p+}Al_{1-x}E_xSi_yO_z$$

where M is at least one exchangeable cation, "m" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation:

$$z=(m \cdot n + r \cdot p + 3 + 4 \cdot y)/2$$

and is characterized in that it has the x-ray diffraction pattern having at least the d spacings and intensities set forth in Table A:

TABLE A

| 2-θ | d(Å) | I/I$_0$ % |
|---|---|---|
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs | b) alkylating benzene with ethylene in the alkylation catalyst bed in the presence of the solid catalyst at alkylation conditions to form ethylbenzene, wherein the alkylation conditions comprise a concentration of ethylene based on the weight of benzene, ethylene, and diethylbenzene passed to the alkylation catalyst bed in Step (a) of at most 10 wt-%; and c) withdrawing an effluent stream comprising ethylbenzene from the alkylation catalyst bed.

25. An alkylation process for producing cumene, the process comprising:

a) passing an aromatic feedstock comprising benzene, an olefinic feedstock comprising propylene, and an aliquot portion of an effluent stream comprising dipropylbenzene to an alkylation catalyst bed containing a solid catalyst, wherein the solid catalyst comprises a microporous crystalline zeolite having a layered framework of at least AlO$_2$ and SiO$_2$ tetrahedral units and a composition on an as-synthesized and anhydrous basis expressed by an empirical formula of:

$$M_m^{n+} R_r^{p+} Al_{1-x} E_x Si_y O_z$$

where M is at least one exchangeable cation, "m" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation:

$$z=(m \cdot n + r \cdot p + 3 + 4 \cdot y)/2$$

and is characterized in that it has the x-ray diffraction pattern having at least the d spacings and intensities set forth in Table A:

TABLE A

| 2-θ | d(Å) | I/I$_0$ % |
|---|---|---|
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs | b) alkylating benzene with propylene in the alkylation catalyst bed in the presence of the solid catalyst at alkylation conditions to form cumene, wherein the alkylation conditions comprise a concentration of propylene based on the weight of benzene, propylene, and dipropylbenzene passed to the alkylation catalyst bed in Step (a) of at most 10 wt-%; and c) withdrawing the effluent stream comprising cumene from the alkylation catalyst bed.

* * * * *